US008088115B2

(12) United States Patent  
Kline et al.

(10) Patent No.: US 8,088,115 B2
(45) Date of Patent: Jan. 3, 2012

(54) REFASTENABLE ABSORBENT ARTICLE AND A METHOD OF APPLYING THEREOF

(75) Inventors: Mark James Kline, Okeana, OH (US); Miguel Alvaro Robles, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/752,826

(22) Filed: Apr. 1, 2010

(65) Prior Publication Data

US 2010/0217221 A1    Aug. 26, 2010

Related U.S. Application Data

(60) Continuation of application No. 12/420,080, filed on Apr. 8, 2009, which is a continuation of application No. 10/291,057, filed on Nov. 8, 2002, now Pat. No. 7,524,313, which is a division of application No. 09/345,653, filed on Jun. 30, 1999, now abandoned, which is a continuation of application No. 09/071,969, filed on May 4, 1998, now Pat. No. 5,957,908, which is a continuation of application No. 08/627,672, filed on Apr. 2, 1996, now Pat. No. 5,897,545.

(51) Int. Cl.
    *A61F 13/15*    (2006.01)
    *A61F 13/20*    (2006.01)
(52) U.S. Cl. .......................... 604/386; 604/389; 604/391
(58) Field of Classification Search ................... 604/386, 604/391, 389
    See application file for complete search history.

(56) References Cited

U.S. PATENT DOCUMENTS

| 2,068,456 A | 1/1937 | Hooper |
| 2,957,512 A | 10/1960 | Wade et al. |
| 3,039,466 A | 6/1962 | Wilson |

(Continued)

FOREIGN PATENT DOCUMENTS

EP    0396050 A2    11/1990

(Continued)

OTHER PUBLICATIONS

Opposition Division, European Patent Office, Decision to Maintain the European patent in Amended Form (Application No. 97916081.9-2314/0959855), Dated Jun. 20, 2007.

(Continued)

*Primary Examiner* — Melanie Hand
(74) *Attorney, Agent, or Firm* — Thibault Fayette

(57) ABSTRACT

Absorbent articles such as disposable diapers, incontinent briefs, diaper holders, training pants and the like, having elastomeric ear panels and a fastening system that provides the user with different options as to how the absorbent article may be fitted to and removed from the wearer. The absorbent articles allow the wearer to choose between conventional and pull-on diaper configurations, or combinations thereof, and properly and comfortably fit a large range of wearer sizes. Further, the absorbent articles can be pulled on and/or off as a pant. This feature is provided by the ear panels which maintain sufficient tension to hold the diaper on the wearer throughout the period of use without harming the wearer's skin, while providing enough stretch to allow the diaper to be pulled up or down over the wearer's hips. The fastening system is refastenable for convenience yet strong enough to maintain the diaper in a fastened configuration without becoming detached if the diaper is pulled on or off the wearer.

18 Claims, 9 Drawing Sheets

U.S. PATENT DOCUMENTS

| | | | |
|---|---|---|---|
| 3,090,097 A | 5/1963 | Ruckstuhl | |
| 3,277,547 A | 10/1966 | Billarant | |
| RE26,152 E | 1/1967 | Andren | |
| 3,316,139 A | 4/1967 | Alford et al. | |
| 3,319,307 A | 5/1967 | Marforio | |
| 3,475,926 A | 11/1969 | Ruckstuhl | |
| 3,577,607 A | 5/1971 | Ikoma et al. | |
| 3,638,651 A | 2/1972 | Torr | |
| 3,694,867 A | 10/1972 | Stumpf | |
| 3,708,833 A | 1/1973 | Ribich et al. | |
| 3,842,832 A | 10/1974 | Wideman et al. | |
| 3,842,837 A | 10/1974 | Sward | |
| 3,848,594 A | 11/1974 | Buell | |
| 3,848,597 A | 11/1974 | Endres | |
| 3,860,003 A | 1/1975 | Buell | |
| 3,911,173 A | 10/1975 | Sprague, Jr. | |
| 3,943,981 A | 3/1976 | De Brabander | |
| 3,955,575 A | 5/1976 | Okuda | |
| 3,994,299 A | 11/1976 | Karami | |
| 4,122,552 A | 10/1978 | Tedford | |
| 4,145,763 A | 3/1979 | Abrams et al. | |
| 4,205,679 A | 6/1980 | Repke et al. | |
| 4,300,967 A | 11/1981 | Sigl | |
| 4,322,875 A | 4/1982 | Brown et al. | |
| 4,409,049 A | 10/1983 | Passafiume et al. | |
| 4,413,623 A | 11/1983 | Pieniak | |
| 4,463,932 A | 8/1984 | Shuker | |
| 4,515,595 A | 5/1985 | Kievit et al. | |
| 4,518,451 A | 5/1985 | Luceri et al. | |
| 4,540,415 A | 9/1985 | Korpman | |
| 4,573,986 A | 3/1986 | Minetola et al. | |
| 4,595,441 A | 6/1986 | Holvoet et al. | |
| 4,596,568 A | 6/1986 | Flug | |
| 4,610,678 A | 9/1986 | Weisman et al. | |
| 4,610,680 A | 9/1986 | Lafleur | |
| 4,610,682 A | 9/1986 | Kopp | |
| 4,615,695 A | 10/1986 | Cooper | |
| 4,624,428 A | 11/1986 | Frank | |
| 4,633,565 A | 1/1987 | Dewoskin | |
| 4,657,802 A | 4/1987 | Morman | |
| 4,662,875 A | 5/1987 | Hirotsu et al. | |
| 4,663,220 A | 5/1987 | Wisneski et al. | |
| 4,673,402 A | 6/1987 | Weisman et al. | |
| 4,701,179 A | 10/1987 | Kellenberger et al. | |
| 4,704,114 A | 11/1987 | Wilson et al. | |
| 4,704,115 A | 11/1987 | Buell | |
| 4,711,683 A | 12/1987 | Merkatoris | |
| 4,761,322 A | 8/1988 | Raley | |
| 4,785,996 A | 11/1988 | Ziecker et al. | |
| 4,834,735 A | 5/1989 | Alemany et al. | |
| 4,834,742 A | 5/1989 | Wilson et al. | |
| 4,842,666 A | 6/1989 | Werenicz | |
| 4,846,815 A | 7/1989 | Scripps | |
| 4,847,134 A | 7/1989 | Fahrenkrug et al. | |
| 4,850,989 A | 7/1989 | Villez | |
| 4,857,067 A * | 8/1989 | Wood et al. | 604/389 |
| 4,869,724 A | 9/1989 | Scripps | |
| 4,880,423 A | 11/1989 | Green | |
| 4,881,997 A | 11/1989 | Hatch | |
| 4,884,323 A | 12/1989 | Provost et al. | |
| 4,888,231 A | 12/1989 | Angstadt | |
| 4,894,060 A * | 1/1990 | Nestegard | 604/391 |
| 4,909,803 A | 3/1990 | Aziz et al. | |
| 4,909,870 A | 3/1990 | Gould et al. | |
| 4,933,224 A | 6/1990 | Hatch | |
| 4,936,840 A | 6/1990 | Proxmire | |
| 4,938,753 A * | 7/1990 | Van Gompel et al. | 604/385.29 |
| 4,938,757 A | 7/1990 | Van Gompel et al. | |
| 4,940,464 A | 7/1990 | Van Gompel et al. | |
| 4,946,527 A | 8/1990 | Battrell | |
| 4,965,278 A | 10/1990 | Horwell et al. | |
| 4,988,344 A | 1/1991 | Reising et al. | |
| 4,988,551 A | 1/1991 | Zegler | |
| 4,998,345 A | 3/1991 | Funahashi et al. | |
| 4,999,067 A | 3/1991 | Erb et al. | |
| 5,000,806 A | 3/1991 | Merkatoris et al. | |
| 5,015,245 A | 5/1991 | Noda | |
| 5,019,065 A | 5/1991 | Scripps | |
| 5,019,073 A | 5/1991 | Roessler et al. | |
| 5,032,122 A | 7/1991 | Noel et al. | |
| 5,057,097 A | 10/1991 | Gesp | |
| 5,058,247 A | 10/1991 | Thomas et al. | |
| 5,062,839 A | 11/1991 | Anderson | |
| 5,069,678 A | 12/1991 | Yamamoto et al. | |
| 5,074,854 A | 12/1991 | Davis | |
| 5,087,253 A | 2/1992 | Cooper | |
| 5,106,385 A | 4/1992 | Allen et al. | |
| 5,125,246 A | 6/1992 | Shytles | |
| 5,143,679 A | 9/1992 | Weber et al. | |
| 5,147,345 A | 9/1992 | Young et al. | |
| 5,147,487 A | 9/1992 | Nomura et al. | |
| 5,151,092 A | 9/1992 | Buell et al. | |
| 5,163,932 A | 11/1992 | Nomura et al. | |
| 5,167,897 A | 12/1992 | Weber et al. | |
| 5,176,670 A | 1/1993 | Roessler et al. | |
| 5,221,274 A | 6/1993 | Buell et al. | |
| 5,226,992 A | 7/1993 | Morman | |
| 5,242,436 A | 9/1993 | Weil et al. | |
| 5,246,433 A | 9/1993 | Hasse et al. | |
| 5,246,656 A | 9/1993 | Stephenson et al. | |
| 5,269,776 A | 12/1993 | Lancaster et al. | |
| 5,296,080 A | 3/1994 | Merkatoris et al. | |
| 5,326,612 A | 7/1994 | Goulait | |
| 5,330,458 A | 7/1994 | Buell et al. | |
| 5,358,500 A | 10/1994 | Lavon et al. | |
| 5,366,452 A | 11/1994 | Widlund et al. | |
| 5,368,584 A * | 11/1994 | Clear et al. | 604/385.29 |
| 5,370,634 A | 12/1994 | Ando et al. | |
| 5,374,262 A | 12/1994 | Keuhn, Jr. et al. | |
| 5,380,313 A | 1/1995 | Goulait et al. | |
| 5,393,599 A | 2/1995 | Quantrille et al. | |
| 5,399,177 A | 3/1995 | Blaney et al. | |
| 5,399,219 A | 3/1995 | Roessler et al. | |
| 5,403,302 A * | 4/1995 | Roessler et al. | 604/391 |
| 5,417,789 A | 5/1995 | Lauritzen | |
| 5,422,172 A | 6/1995 | Wu | |
| 5,454,803 A | 10/1995 | Sageser et al. | |
| 5,460,622 A | 10/1995 | Dragoo et al. | |
| 5,462,540 A | 10/1995 | Caldwell | |
| 5,476,458 A | 12/1995 | Glaug et al. | |
| 5,496,298 A | 3/1996 | Kuepper et al. | |
| 5,496,428 A | 3/1996 | Sageser et al. | |
| 5,527,302 A | 6/1996 | Endres et al. | |
| 5,531,732 A | 7/1996 | Wood | |
| 5,542,943 A | 8/1996 | Sageser | |
| 5,545,159 A | 8/1996 | Lancaster et al. | |
| 5,554,145 A | 9/1996 | Roe et al. | |
| 5,569,234 A | 10/1996 | Buell et al. | |
| 5,575,784 A | 11/1996 | Ames-Ooten et al. | |
| 5,576,090 A | 11/1996 | Suzuki | |
| 5,577,540 A | 11/1996 | Sageser | |
| 5,580,411 A | 12/1996 | Nease et al. | |
| 5,591,155 A | 1/1997 | Nishikawa et al. | |
| 5,595,567 A | 1/1997 | King et al. | |
| 5,624,420 A | 4/1997 | Bridges et al. | |
| 5,624,427 A | 4/1997 | Bergman et al. | |
| H1674 H | 8/1997 | Ames et al. | |
| 5,660,666 A | 8/1997 | Dilnik et al. | |
| 5,669,996 A | 9/1997 | Jessup | |
| 5,683,533 A | 11/1997 | Keighley et al. | |
| 5,685,873 A | 11/1997 | Bruemmer | |
| 5,685,874 A | 11/1997 | Buell et al. | |
| 5,693,165 A | 12/1997 | Schmitz | |
| 5,695,488 A | 12/1997 | Sosalla | |
| 5,705,013 A | 1/1998 | Nease et al. | |
| 5,722,127 A | 3/1998 | Coates | |
| 5,722,968 A | 3/1998 | Datta et al. | |
| 5,725,714 A | 3/1998 | Fujioka et al. | |
| 5,735,840 A | 4/1998 | Kline et al. | |
| 5,746,730 A | 5/1998 | Suzuki et al. | |
| 5,776,123 A | 7/1998 | Goerg et al. | |
| 5,830,206 A | 11/1998 | Larsson | |
| 5,836,931 A | 11/1998 | Toyoda et al. | |
| 5,843,068 A | 12/1998 | Allen et al. | |
| 5,846,262 A | 12/1998 | Sayama et al. | |
| 5,846,365 A | 12/1998 | Kline et al. | |
| 5,853,405 A | 12/1998 | Suprise | |

| | | | |
|---|---|---|---|
| 5,855,574 A | 1/1999 | Kling et al. | |
| 5,873,868 A | 2/1999 | Nakahata | |
| 5,873,870 A | 2/1999 | Seitz et al. | |
| 5,897,545 A | 4/1999 | Kline et al. | |
| 5,899,895 A | 5/1999 | Robles et al. | |
| 5,899,896 A | 5/1999 | Suprise et al. | |
| 5,928,212 A | 7/1999 | Kline et al. | |
| 5,957,908 A | 9/1999 | Kline et al. | |
| 5,961,761 A | 10/1999 | Heindel et al. | |
| 6,004,306 A | 12/1999 | Robles et al. | |
| 6,030,373 A | 2/2000 | Vangompel et al. | |
| 6,120,489 A | 9/2000 | Johnson et al. | |
| 6,142,985 A | 11/2000 | Feist | |
| 6,149,639 A | 11/2000 | Lundberg et al. | |
| RE37,145 E | 4/2001 | Barenboim et al. | |
| 6,210,388 B1 | 4/2001 | Widlund et al. | |
| 6,230,374 B1 | 5/2001 | Widlund | |
| 6,240,569 B1 | 6/2001 | Van Gompel et al. | |
| 6,248,526 B1 | 6/2001 | Weimer | |
| 6,273,165 B1 | 8/2001 | Gundersen et al. | |
| 6,328,725 B2 | 12/2001 | Fernfors | |
| 6,340,782 B1 | 1/2002 | Kling et al. | |
| 6,375,646 B1 | 4/2002 | Widlund et al. | |
| 6,428,526 B1 | 8/2002 | Heindel et al. | |
| 6,461,344 B1 | 10/2002 | Widlund et al. | |
| 6,491,676 B1 | 12/2002 | Suzuki et al. | |
| 6,494,872 B1 | 12/2002 | Suzuki et al. | |
| 6,534,694 B2 | 3/2003 | Kling et al. | |
| 6,849,067 B2 | 2/2005 | Fletcher et al. | |
| 6,994,698 B2 | 2/2006 | Leak et al. | |
| 7,524,313 B2 | 4/2009 | Kline et al. | |
| 2002/0188268 A1 | 12/2002 | Kline et al. | |
| 2008/0125736 A1 | 5/2008 | Kline et al. | |
| 2009/0198206 A1 | 8/2009 | Kline et al. | |

FOREIGN PATENT DOCUMENTS

| | | |
|---|---|---|
| EP | 0396512 A2 | 11/1990 |
| EP | 0417766 A1 | 3/1991 |
| EP | 0 433 951 A2 | 6/1991 |
| EP | 0 456 281 A2 | 11/1991 |
| EP | 0455231 A1 | 11/1991 |
| EP | 0 528 282 A3 | 2/1993 |
| EP | 0 532 034 A2 | 3/1993 |
| EP | 0567792 A1 | 3/1993 |
| EP | 0 570 980 A1 | 11/1993 |
| EP | 0587196 A1 | 3/1994 |
| EP | 0589859 A1 | 3/1994 |
| EP | 0597331 A1 | 5/1994 |
| EP | 0 600 494 A1 | 6/1994 |
| EP | 0 605 012 A1 | 7/1994 |
| EP | 0605013 A1 | 7/1994 |
| EP | 0700675 A1 | 3/1996 |
| EP | 0743052 A2 | 11/1996 |
| FR | 2 606 257 | 5/1988 |
| FR | 2606257 | 5/1988 |
| GB | 2 244 422 | 4/1991 |
| GB | 2 245 149 A | 1/1992 |
| GB | 2 267 024 A | 11/1993 |
| GB | 2 267 024 A | 11/1993 |
| GB | 2285208 A1 | 7/1995 |
| GB | 2 308 290 A | 6/2007 |
| JP | 59-129805 | 8/1984 |
| JP | 59-129805 A1 | 8/1984 |
| JP | 01-168905 A | 7/1989 |
| JP | 02-004367 | 1/1990 |
| JP | 03-176053 | 7/1991 |
| JP | 03-195555 | 8/1991 |
| JP | 04-28364 | 1/1992 |
| JP | 04-044920 | 4/1992 |
| JP | 04-144558 | 5/1992 |
| JP | 04-161152 | 6/1992 |
| JP | 04-261655 | 9/1992 |
| JP | 04-354948 | 12/1992 |
| JP | 05-31135 | 2/1993 |
| JP | 05-76566 | 3/1993 |
| JP | 05-137746 | 6/1993 |
| JP | 06-000204 | 1/1994 |
| JP | 06-005562 | 1/1994 |
| JP | 06-114084 | 4/1994 |
| JP | 06-055623 U | 8/1994 |
| JP | 06-285113 | 10/1994 |
| JP | 06-296643 | 10/1994 |
| JP | 1994285113 A | 10/1994 |
| JP | 07-75653 | 3/1995 |
| JP | 07-80023 | 3/1995 |
| JP | 7-252762 | 10/1995 |
| JP | 08-56986 | 3/1996 |
| JP | 08-56988 | 3/1996 |
| JP | 2006-055669 A | 3/2006 |
| TW | 261765 | 1/1995 |
| WO | WO 90/07313 A1 | 7/1990 |
| WO | WO 91/08725 A1 | 6/1991 |
| WO | WO 92/20251 | 11/1992 |
| WO | WO 93-24085 A1 | 12/1993 |
| WO | WO 95-00096 A1 | 1/1995 |
| WO | WO 95/03765 A3 | 2/1995 |
| WO | WO 95/05140 A1 | 2/1995 |
| WO | WO 95-12491 A1 | 5/1995 |
| WO | WO 95/13775 A1 | 5/1995 |
| WO | WO 95-19753 A1 | 7/1995 |
| WO | WO 95/22951 A1 | 8/1995 |
| WO | WO 95-27460 A1 | 10/1995 |
| WO | WO 95-27462 A1 | 10/1995 |
| WO | WO 95-27463 A1 | 10/1995 |
| WO | WO 95/29657 A1 | 11/1995 |
| WO | WO 95-32695 A1 | 12/1995 |
| WO | WO 95-32696 A1 | 12/1995 |
| WO | WO 95/34266 A1 | 12/1995 |
| WO | WO 96-05788 A1 | 2/1996 |
| WO | WO 96-14815 A1 | 5/1996 |
| WO | WO 96/19960 A1 | 7/1996 |
| WO | WO 96-24319 A1 | 8/1996 |
| WO | WO 96-31179 A2 | 10/1996 |
| WO | WO 96-35402 A1 | 11/1996 |
| WO | WO 97-02796 A1 | 1/1997 |
| WO | WO 97-02799 A1 | 1/1997 |
| WO | WO 97-09953 A1 | 3/1997 |
| WO | WO 97-16146 A1 | 5/1997 |
| WO | WO 97-18785 A1 | 5/1997 |
| WO | WO 97-28774 A1 | 8/1997 |
| WO | WO 97-30671 A2 | 8/1997 |
| WO | WO 97-32552 A1 | 9/1997 |
| WO | WO 97-34555 A1 | 9/1997 |
| WO | WO 97-34556 A2 | 9/1997 |
| WO | WO 9736566 A1 * | 10/1997 |
| WO | WO 97-46197 A1 | 12/1997 |

OTHER PUBLICATIONS

European Patent Office, Grounds for the decision (Annex) (Application No. 97 916 081.9).

Graham Boon, Elkington and Fife, LLP, Response to Notice of Opposition (European Patent Application No. 97916081.9), dated Mar. 18, 2004.

Graham Boon, Elkington and Fife, LLP, Grounds of Appeal on Behalf of the Patentee (Appeal Case T0489/05-326), dated Jul. 4, 2005).

European Patent Office, Notice of Opposition to a European Patent, Patent No. EP 0959855 B1, dated Nov. 27, 2002.

C.R. Davies, Frank B. Dehn & Co., Notice of Opposition and Statement of Facts and Arguments (in re: European Patent No. 0959855B1), dated Aug. 27, 2003.

Photographs labeled, "L-78338-00/LB-858 Huggies Supreme Step 4 (Read II)", 8 pages.

Albihns, Notice of Opposition (in re: European Patent EP-B-0 959 855,), dated Aug. 21, 2003.

U.S. Appl. No. 08/627,672, filed Apr. 2, 1996, Notice of Allowance dated Dec. 16, 1998.

U.S. Appl. No. 08/627,672, filed Apr. 2, 1996, Office Action dated Aug. 31, 1998.

U.S. Appl. No. 08/627,672, filed Apr. 2, 1996, Office Action dated Mar. 20, 1998.

U.S. Appl. No. 08/627,672, filed Apr. 2, 1996, Office Action dated Sep. 5, 1997.

U.S. Appl. No. 09/071,969, filed May 4, 1998, Office Action dated Jan. 21, 1999.

U.S. Appl. No. 09/071,969, filed May 4, 1998, Notice of Allowance dated May 4, 1999.
U.S. Appl. No. 09/345,653, filed Jun. 30, 1999, Office Action dated Aug. 13, 2002.
U.S. Appl. No. 09/345,653, filed Jun. 30, 1999, Office Action dated Apr. 30, 2002.
U.S. Appl. No. 09/345,653, filed Jun. 30, 1999, Office Action dated Aug. 15, 2001.
U.S. Appl. No. 10/291,057, filed Nov. 8, 2002, Notice of Allowance dated Dec. 23, 2008.
U.S. Appl. No. 10/291,057, filed Nov. 8, 2002, Notice of Allowance dated Jul. 14, 2008.
U.S. Appl. No. 10/291,057, filed Nov. 8, 2002, Notice of Allowance dated Nov. 28, 2007.
U.S. Appl. No. 10/291,057, filed Nov. 8, 2002, Office Action dated May 16, 2007.
U.S. Appl. No. 10/291,057, filed Nov. 8, 2002, Office Action dated Nov. 1, 2006.
U.S. Appl. No. 10/291,057, filed Nov. 8, 2002, Office Action dated Jul. 14, 2006.
U.S. Appl. No. 10/291,057, filed Nov. 8, 2002, Office Action dated Nov. 23, 2005.
U.S. Appl. No. 10/291,057, filed Nov. 8, 2002, Office Action dated Jul. 12, 2005.
U.S. Appl. No. 10/291,057, filed Nov. 8, 2002, Office Action dated Jan. 27, 2005.
U.S. Appl. No. 10/291,057, filed Nov. 8, 2002, Office Action dated Jun. 1, 2004.
U.S. Appl. No. 10/291,057, filed Nov. 8, 2002, Office Action dated Aug. 29, 2003.
U.S. Appl. No. 11/250,255, filed Oct. 14, 2005, Reply to Office Action dated Aug. 5, 2009.
U.S. Appl. No. 11/250,255, filed Oct. 14, 2005, Office Action dated Aug. 5, 2009.
U.S. Appl. No. 11/250,255, filed Oct. 14, 2005, Reply to Office Action dated Jan. 29, 2009.
U.S. Appl. No. 11/250,255, filed Oct. 14, 2005, Office Action dated Jan. 29, 2009.
U.S. Appl. No. 11/250,255, filed Oct. 14, 2005, Notice of Allowance dated Jan. 11, 2010.
U.S. Appl. No. 90/006,775, filed Sep. 12, 2003, Re-Examination of U.S. 6,428,526.
Reexamination of U.S. Appl. No. 95/001,228 Inter Parte Re-examination of U.S. Patent 6,849,067.
U.S. Appl. No. 12/752,843, filed Apr. 1, 2010—Office Action dated Jan. 25, 2011 and Response dated Apr. 25, 2011 (32 pages).
U.S. Appl. No. 12/752,855, filed Apr. 1, 2010—Office Action dated Apr. 15, 2011 and Responses dated May 26, 2011 (27 pages).
U.S. Appl. No. 12/752,863, filed Apr. 1, 2010—Office Actions dated Sep. 1, 2010 and Apr. 1, 2011 and Response dated Jan. 14, 2011 (48 pages).
U.S. Appl. No. 12/752,874, filed Apr. 1, 2010—Office Action dated Mar. 3, 2011 and Response dated Apr. 25, 2011 (31 pages).
U.S. Appl. No. 12/752,883, filed Apr. 1, 2010—Office Actions dated Oct. 5, 2010 and Mar. 30, 2011 and Response dated Jan. 14, 2011 (47 pages).
U.S. Appl. No. 12/752,890, filed Apr. 1, 2010—Office Action dated Apr. 27, 2011 and Response dated Jun. 21, 2011 (27 pages).
U.S. Appl. No. 12/752,894, filed Apr. 1, 2010—Office Action dated Apr. 27, 2011 and Response dated May 26, 2011 (47 pages).
U.S. Appl. No. 12/752,912, filed Apr. 1, 2010—Office Action dated May 25, 2011 and Response dated Jun. 13, 2011 (30 pages).

* cited by examiner

REFASTENABLE ABSORBENT ARTICLE AND A METHOD OF APPLYING THEREOF

CROSS-REFERENCE TO RELATED APPLICATION

This application is a continuation of U.S. application Ser. No. 12/420,080, filed on Apr. 8, 2009, which is a continuation application of U.S. application Ser. No. 10/291,057, filed on Nov. 8, 2002, now U.S. Pat. No. 7,524,313 issued Apr. 28, 2009, which is a divisional of the parent application U.S. Ser. No. 09/345,653 filed Jun. 30, 1999, now abandoned, which is a continuation of the patent application U.S. Ser. No. 09/071,969 filed May 4, 1998, now U.S. Pat. No. 5,957,908 issued Sep. 28, 1999, which is a continuation of the patent application U.S. Ser. No. 08/627,672 filed Apr. 2, 1996, now U.S. Pat. No. 5,897,545 issued Apr. 27, 1999.

FIELD OF INVENTION

The present invention relates to absorbent articles such as diapers, incontinence briefs, diaper holders, training pants and the like, and more particularly, to absorbent articles having elastomeric ear panels and a fastening system that provides the user with different options as to how the diaper will be fitted to the wearer.

BACKGROUND OF THE INVENTION

Infants and other incontinent individuals wear absorbent articles such as diapers to receive and contain urine and other body exudates. Absorbent articles function both to contain discharged materials and to isolate the materials from the body of the wearer and from the wearer's garments and bed clothing. Disposable absorbent articles having many different basic designs are known to the art. For example, U.S. Pat. Re. 26,152, entitled "Disposable Diaper" issued to Duncan and Baker on Jan. 31, 1967 describes a conventional disposable diaper which has achieved worldwide acceptance and commercial success. Further, U.S. Pat. No. 5,246,433 entitled "Elasticized Disposable Training Pant And Method of Making The Same" issued to Hasse et al. on Sep. 21, 1993 discloses a unitary disposable absorbent article that can be used as a training pant.

In the market today, the consumer has a number of different basic diaper designs to choose from depending on the desired options, comfort and cost, including conventional diapers, belted diapers, and "pull-on" type diapers or training pants. However, many of the absorbent articles on the market today are capable of fitting only a small range of wearer sizes and therefore, the consumer must continually monitor the size of the wearer to determine which diaper will comfortably and effectively fit the wearer. Further, most commercially available diapers are limited in that they can only effectively be used in one of the above-mentioned configurations without any of the benefits attributable to any of the other diaper types. Thus, the consumer must purchase different diapers depending on the desired characteristics for the intended use.

Conventional diaper designs are generally the least expensive type of absorbent article to produce and are generally acceptable for use on babies and persons who are sick or otherwise confined to a bed. A conventional diaper is fitted to the wearer by first placing a portion of the diaper under the wearer (generally, the back portion of the diaper is placed under the buttocks and rear waist of the wearer) and then pulling the remainder of the diaper through the wearer's legs. The rear portion of the diaper is then attached to the front portion of the diaper on each side of the wearer. However, such conventional configurations tend to be very difficult to use when the wearer refuses to remain still throughout the period of application. Further, adult wearers and children in their toilet training stage often find the conventional type absorbent articles difficult to put on themselves without assistance.

The "pull-on" design absorbent article is often used in training pants and incontinence briefs. The "pull-on" design allows the wearer to pull the absorbent article on as pants and does not require any of the fastening steps of the conventional or belted type absorbent article designs. Although this feature is desirable for many adult users and children in their toilet training stage, the "pull-on" design is impractical for many users, especially those bed ridden and small children unable to dress themselves. Pull-on absorbent articles generally lack any features that allow the diaper to be put on, removed or checked for soiling without removal of the diaper and the wearer's outer clothing. Further, such articles often lack features that allow for convenient, sanitary disposal of the article.

The present invention combines the benefits of a conventional diaper with those of a "pull-on" type diaper. Further, the diaper of the present invention can comfortably and effectively fit a large range of wearer sizes. These unique characteristics are provided by the inventive coordination of special ear panels and fastening elements. The ear panels and fastening elements work together to solve the problems encountered in earlier attempts to provide some of the features of the present invention. For example, the present invention can be fitted to a wide range of wearers in the conventional configuration and provide excellent containment and comfort characteristics due to the ability of the ear panels to provide a snug fit when fitted to small wearers as well as a snug comfortable fit to much larger wearers. The refastenable fastening system provides a strong closure that can withstand the dynamic forces created by the motions of the wearer; the forces generally being different depending on the size and age of the wearer. Further, structural design of the diaper provides the user with the opportunity to use the diaper as a pull-on. The unique ear panels provide the necessary stretch to effectively accommodate a large range of wearers as well as the stretch needed to provide for easy application as a pull up diaper. Again, the fastening system complements the ear panels to provide a strong closure, yet still provides a means for removing the pull-on by opening the closures rather than pulling the diaper down over the hips of the wearer. This makes the removal of a soiled diaper a much quicker and cleaner without the need to remove the wearer's clothing. Furthermore, the refastenable fastening system provides a pull-on user with the ability to check for soiling of the diaper by opening one or more of the closures rather than removing the diaper completely. Also, the absorbent article of the present invention can easily be configured with a disposal feature (often the fastening system) which provides a convenient, sanitary means for disposing of the soiled article.

In the past, diapers designs attempting to provide the benefits described above have been generally unable to solve the problems associated with providing a diaper that effectively and comfortably fits a large range of wearer sizes as well as provides at least two ways in which the diaper may be constructed and fit to the wearer. In attempting to fit a large range of wearers, previous diaper designs (both conventional and pull-on) have generally been loose and ineffective containing the waste of small wearers while being extremely tight, uncomfortable and unable to withstand the dynamic forces produced by large wearers. Further, many pull-on designs lacked any means for checking the diaper for soiling without removal of the diaper and often the wearer's clothing. Likewise, pull-on designs generally lack any means for removing a soiled diaper without having to tear one or more elements (generally seams) of the diaper which can renders the diaper useless if checked for soiling. Also, pull-on diapers generally lack any means for convenient disposal.

Therefore, it would be beneficial to provide an absorbent article having a refastenable fastening system and stretchable ear panels designed to allow the absorbent article to be fitted to the wearer in a conventional or "pull-on" configuration.

It is also would be beneficial to provide an absorbent article that will effectively and comfortably fit a large range of wearer sizes in either a conventional or a pull-on configuration.

It is still would be beneficial to provide a diaper that can be fitted to a wearer or removed as a pull-on or a conventional diaper.

These and other objects of the present invention will be more readily apparent when considered in reference to the following description and when taken in conjunction with the accompanying drawings.

SUMMARY OF THE INVENTION

In one preferred embodiment of the present invention, an absorbent article is provided having a longitudinal centerline and a lateral centerline, the absorbent article comprising a containment assembly having a rear waist region, a crotch region, a front waist region, a pair of longitudinal edges, a body facing surface and a garment facing surface opposite of the body facing surface. The containment assembly comprises a topsheet, a backsheet joined to the topsheet, and an absorbent core positioned between the topsheet and the backsheet. The absorbent article may further comprise an elastomeric first ear panel extending laterally outwardly from one of the longitudinal edges of the containment assembly in the rear waist region, the first ear panel having a proximal edge joined with the containment assembly, a distal edge spaced laterally outwardly from the proximal edge, an inner surface, and an outer surface. The absorbent article may further comprise an elastomeric second ear panel extending laterally outwardly from the other of the longitudinal edges of the containment assembly in the rear waist region, the second ear panel having a proximal edge joined with the containment assembly, a distal edge spaced laterally outwardly from the proximal edge, an inner surface, and an outer surface.

The absorbent article may further comprise a refastenable mechanical fastening system. The refastenable mechanical fastening system comprises a first closure member disposed adjacent the distal edge ear of the first ear panel and a second closure member disposed adjacent the distal edge of the second ear panel. The first closure member and the second closure member each comprise a single engaging component having a laterally outboard longitudinal edge and a laterally inboard longitudinal edge, the laterally inboard longitudinal edge being nonuniform and having portions extending laterally inboard to define two laterally inboard points. The first closure member and the second closure member each have a closure member major axis extending between the two laterally inboard points, the closure member major axis being at an angle to the longitudinal and the lateral centerline of the absorbent article. The refastenable mechanical fastening system may further comprise a third closure member disposed in the front waist region on the garment facing surface of the containment assembly, the third closure member engageable with the first closure member and the second closure member so as to define a waist hoop having a relaxed state circumference.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

Figure 1:
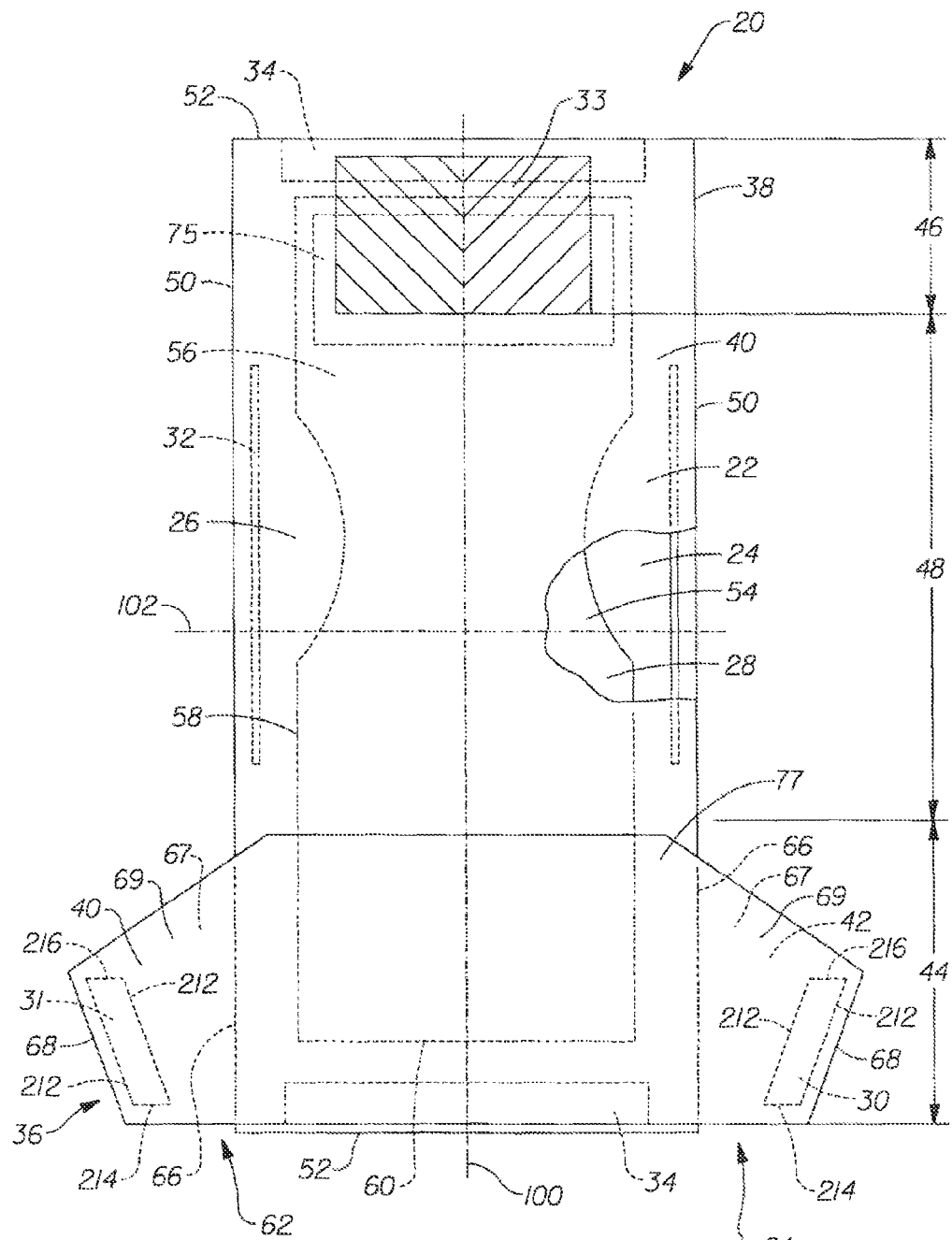
FIG. 1 is a plan view of a disposable diaper embodiment of the present invention having portions cut away to reveal underlying structure, the outer surface of the diaper is facing the viewer.

FIG. 1 is a plan view of the diaper 20 of a preferred embodiment of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the garment facing surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The diaper 20 preferably further comprises elasticized leg cuffs 32; an waist features 34; a first ear panel 62; a second ear panel 64; and a fastening system 200 comprising a first closure member 30, a second closure member 31 and a third closure member 33. The diaper 20 may also comprise front ear flaps 38, a landing zone reinforcing member 75 and disposal means 77

The diaper 20 is shown in FIG. 1 to have an garment facing surface 40 (facing the viewer in FIG. 1), an body facing surface 42 opposed to the garment facing surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the longitudinal edges are designated 50 and the end edges are designated 52. The body facing surface 42 of the diaper 20 comprises that portion of the diaper 20 which is positioned adjacent to the wearer's body during use (i.e., the body facing surface 42 generally is formed by at least a portion of the topsheet 24 and other components joined to the topsheet 24). The garment facing surface 40 comprises that portion of the diaper 20 which is positioned away from the wearer's body (i.e., the garment facing surface 40 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48. The rear waist region 44 comprises two ear panels, the first ear panel 62, and the second ear panel 64, which typically comprise the outer lateral portions of the rear waist region 44. The front waist region 46 may also include a pair of front ear flaps designated 38, which typically comprise the outer lateral portions of the front waist region 46.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

In a preferred embodiment of the present invention, the containment assembly 22 comprises a topsheet 24 and a backsheet 26 which have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side 54, a body-facing side 56, a pair of side edges designated 58, and a pair of waist edges designated 60. One embodiment of the diaper 20 has an asymmetric, modified T-shaped absorbent core 28 having ears in the front waist region 46 but a generally rectangular shape in the rear waist region 44. However, the absorbent core 28 may be manufactured in a wide variety of sizes and shapes (e.g., rectangular, hourglass, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat.

No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, et al., on Sep. 15, 1992. All of these patents are incorporated herein by reference.

The backsheet 26 is positioned adjacent the garment-facing surface 54 of the absorbent core 28 and is preferably joined thereto by attachment means such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., marketed as HL-1258, and Findley Adhesives Corporation of Wauwatosa, Wis., marketed as Findley 2031. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art. Embodiments of the present invention are also contemplated wherein the absorbent core is not joined to the backsheet 26, the topsheet 24, or both in order to provide greater extensibility throughout the diaper 20.

The backsheet 26 is preferably impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. However, the backsheet 26 is preferably breathable so as to permit vapors to escape from the absorbent core 28 while still preventing exudates from passing through the backsheet 26. Thus, the backsheet 26 preferably comprises a woven or nonwoven material, polymeric films such as thermoplastic films of polyethylene or polypropylene, or composite materials such as a film-coated nonwoven material. A suitable backsheet 26 is a thermoplastic film having a thickness of from about 0.012 mm (0.5 mil) to about 0.051 mm (2.0 mils) joined with a nonwoven covering comprising natural or synthetic fibers. If the backsheet 26 is a film, it is preferably embossed and/or matte finished to provide a more clothlike appearance.

In preferred embodiments of the present invention, at least a portion of the backsheet 26 is subjected to mechanical stretching in order to provide both a "zero strain" stretch laminate that forms the portion of the backsheet 26 coinciding with the waist feature 34. The backsheet 26 can be prestrained by directing the backsheet through an incremental mechanical stretching system similar to the operation described with respect to the formation of the "zero strain" stretch laminate backsheet and elasticized ear panels in U.S. Pat. No. 5,151,092 entitled "Absorbent Article With Dynamic Elastic Waist Feature Having A Predisposed Resilient Flexural Hinge", issued to Buell et al., on Sep. 29, 1992. Accordingly, the backsheet is preferably elongatable, more preferably drawable, but not necessarily elastomeric, so that the backsheet 26 will, upon mechanical stretching, be at least to a degree permanently elongated such that it will not fully return to its original undistorted configuration. In preferred embodiments, the backsheet 26 can be subjected to mechanical stretching without undue rupturing or tearing. Thus, it is preferred that the backsheet 26 have an ultimate elongation to break of at least 200% to about 700% in the cross-machine direction as measured using a method consistent with ASTM (American Society of Testing Materials) D-638. Films suitable for use as the backsheet 26 generally contain a high content of linear low density polyethylene. The Clopay Corporation of Cincinnati, Ohio, manufactures a suitable backsheet under the designation 1401. Other suitable materials for the backsheet 26 include RR8220 blown films and RR5475 cast films as manufactured by Tredegar Industries, Inc. of Terre Haute, Ind.

Alternatively, the backsheet 26, or any portion thereof, may comprise a structural elastic-like film (SELF) web. A structural elastic-like film web is an extensible material that exhibits an elastic-like behavior in the direction of elongation without the use of added elastic materials. The SELF web includes a strainable network having at least two contiguous; distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region.

The strainable web material is preferably comprised substantially of linear low density polyethylene (LLDPE). The strainable web material may also be comprised of other polyolefins such as polyethylenes, including low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to polyester, polyurethanes, compostable or biodegradable polymers, heat shrink polymers, thermoplastic elastomers, and breathable polymeric structures. SELF webs suitable for the present invention are more completely described in the copending, commonly assigned European Patent Application WO 9503765 entitled "Web materials Exhibiting Elastic-Like Behavior", published Feb. 9, 1995 in the names of Chappel et al., which is incorporated herein by reference.

The size of the backsheet 26 is dictated by the size of the absorbent core 28 and the exact diaper design selected. In one embodiment, the backsheet 26 has a modified hourglass shape extending beyond the absorbent core a minimum distance of about 1 cm to about 5 cm (about 0.5 inch to about 2 inch) around the entire diaper periphery.

The topsheet 24 is positioned adjacent the body-facing surface 56 of the absorbent core 28 and is preferably joined thereto and to the backsheet 26 by attachment means such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery. The topsheet 24 is preferably compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of the present invention, at least a portion of the topsheet 24 is subjected to mechanical stretching in order to provide a "zero strain" stretch laminate that forms the waist features 34. The topsheet 24 can be pre-strained by any methods as are known in the art including, but not limited to, the methods described herein with respect to the formation of the "zero strain" stretch backsheet. Thus, the topsheet 24 is preferably elongatable, more preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupture or tearing. Thus, it is preferred that the topsheet 24 have a low cross-machine direction (lateral direction) yield strength.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wet-laid, melt-blown, hydroentangled, combinations of the above, or the like. A suitable topsheet 24 is carded and thermally bonded by means well known to those skilled in the art. A satisfactory topsheet 24 comprises staple length polypropylene fibers having a denier of about 2.2 As used herein, the term "staple length fibers" refers to those fibers having a length of at least about 15.9 mm (0.625 inches). Preferably, the topsheet 24 has a basis weight from about 14 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waste Containment Garment" issued to Buell on Nov. 3, 1987, discloses a disposable diaper or incontinence garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, each elasticized leg cuff 32 preferably comprises a gasketing cuff as described in the above-referenced U.S. Pat. No. 3,860,003 and a barrier cuff as described in the above-referenced U.S. Pat. No. 4,909,803.

The diaper 20 may also comprise front ear flaps 38 that extend laterally outwardly from each longitudinal edge 50 of the containment assembly 22 in the front waist region 46. The front ear flaps 38 provide a structure that the user may hold while fastening the diaper 20 about the wearer in a conventional diaper configuration. The front ear flaps 38 may take on a number of different sizes, shapes, configurations, and materials. The front ear flaps 38 may comprise a portion of the material making up one or more of the diaper elements, including the topsheet 24, and the backsheet 26. Alternatively, the front ear flaps 38 may comprise a separate element or a plurality of elements affixed to the diaper. Further, the front ear flaps 38 may comprise extensible or non-extensible material. Suitable materials for use in the front ear flaps 38 include woven webs; nonwoven webs; films, including polymeric films; foams; laminate materials including film laminates, nonwoven laminates, or zero strain laminates; formed films; elastomers; composites; structural elastic like-film (SELF) webs or any combination of materials hereinafter described or as described with respect to the extensible ear panels 62 and 64 as are known in the art. The front ear flaps 38 may be joined to the containment assembly 22 by any means as known in the art; for example the front ear flaps 38 may be continuously or intermittently bonded to the containment assembly 22 using adhesive, heat bonding, pressure bonding, ultrasonic bonding, dynamic mechanical bonding or any other method that is known in the art.

Figure 4:
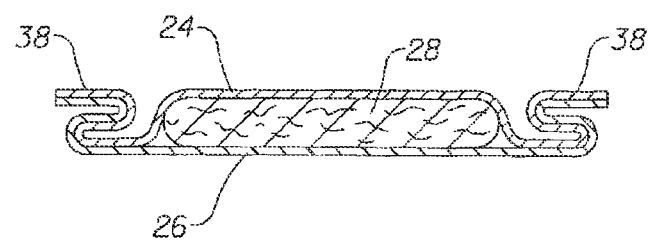
FIG. 4 is a cross-sectional view of a portion of the front waist region one embodiment of the present invention having a front ear flap in a folded configuration.
Figure 5:
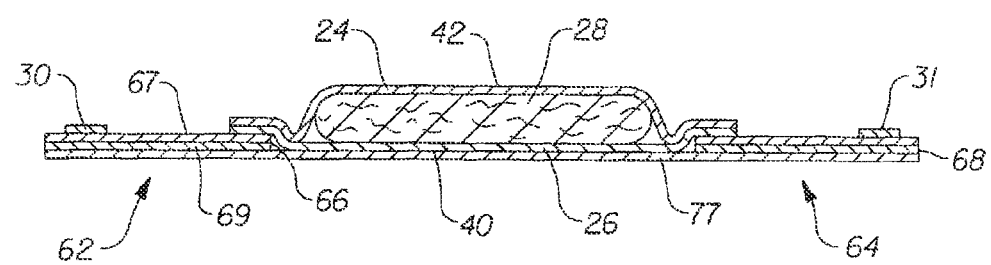
FIG. 5 is a cross-sectional view of a portion of the rear waist region of one embodiment of the present invention.

In one preferred embodiment, the front ear flaps 38 are folded as shown in FIG. 4. The folded front ear flaps 38 may be preferred by some users when the diaper is used in its pull-on capacity. With the front ear flaps 38 in their folded configuration, it is less likely that they will interfere with the stretch of the ear panels 62 and 64 as the diaper 20 is pulled on or off. The front ear flaps 38 may be releasably bonded in their folded configuration such that they can be extended to their open configuration if desired. (As used herein, the term "open configuration" refers to the front ear flaps 38, when they are partially or fully extended from their folded configuration to extend laterally outwardly from the containment assembly 22.) The releasable bonds may comprise any bonding means as is known in the art, including, but not limited to, those bonding means described above with regard to the front ear flaps 38, as well as friction, static or any other bonding means or combination of bonding means.

The diaper 20 preferably further comprises a waist feature 34 that helps provide improved fit and containment. The waist feature 34 may be elastically extensible or inelastic. In preferred embodiments, the waist feature 34 has at least some ability to expand and contract in conjunction with wearer's motions. The waist feature 34 preferably extends longitudinally outwardly from at least one of the waist edges 60 of the absorbent core 28 and generally forms at least a portion of the end edge 52 of the diaper 20. Disposable diapers are generally constructed so as to have two waist features, one positioned in the rear waist region 44 and one positioned in the front waist region 46, although diapers can be constructed with a single waist feature. Further, while the waist feature 34 or any of its constituent elements can comprise a separate element affixed to the diaper 20, the waist feature 34 may be constructed as an extension of other elements of the diaper such as the backsheet 26 or the topsheet 24, preferably both the backsheet 26 and the topsheet 24.

The waist feature 34 may comprise any material suitable for application in a garment to be fitted to a wearer. If the waist feature 34 is to be elastic, any suitable stretchable or elastomeric materials may be used. (As used herein, the term "stretchable" refers to materials that are extensible when forces are applied to the material, and offer some resistance to extension. The terms "elastomeric" or "elastically extensible" refer to materials that extend in at least one direction when a force is applied to the material, and return to approximately their original dimensions after the force is released.) Suitable elastomeric materials for use as the waist feature 34 are described hereinbelow with respect to the extensible ear panels 62 and 64.

The waist feature 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference. Further, the waist feature 34 may comprise "pleats" that may be activated by the diaperer to provide additional extension in the waist regions. (As used herein, the term "pleats" refers to regions of material that have been folded back upon themselves such that when an activation force is applied the material unfolds.)

Figure 3:
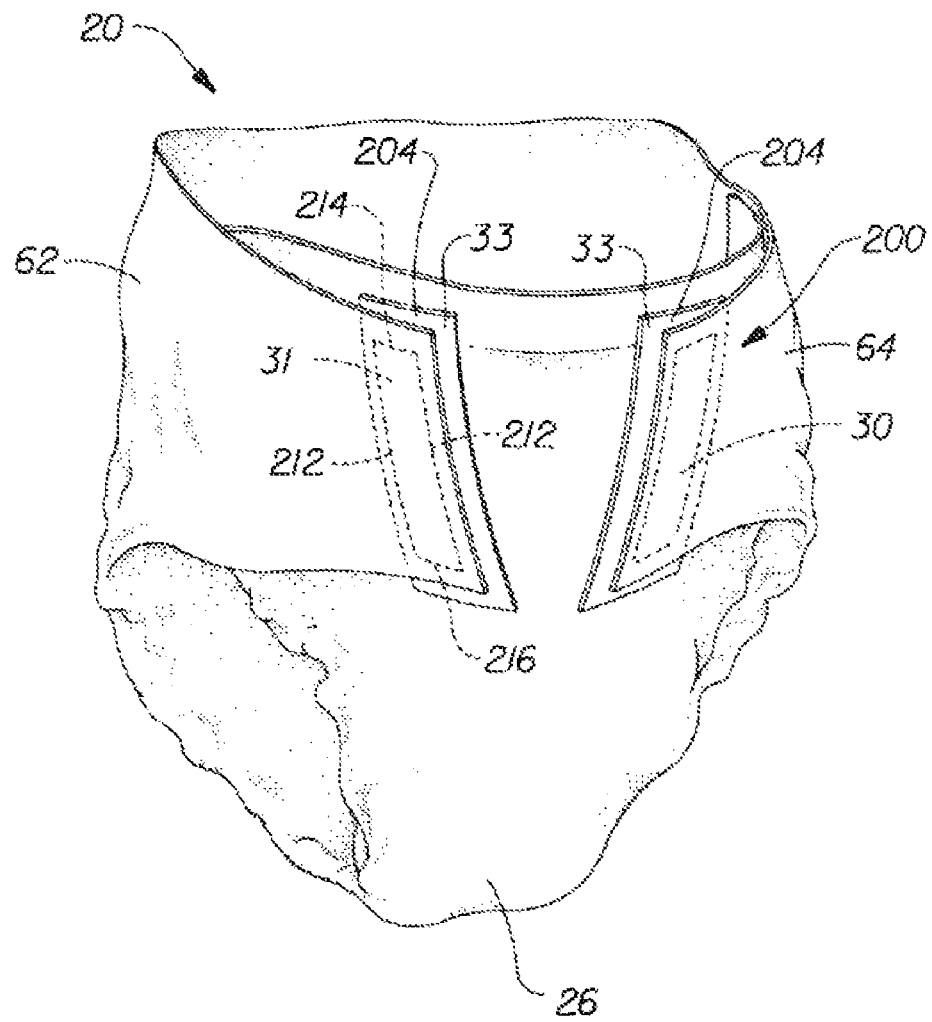
FIG. 3 is a perspective view of one embodiment of the present invention in its pull-on configuration.

The diaper 20 additionally comprises a pair of flaps disposed in at least a portion of the rear waist region 44 such as first ear panel 62 and second ear panel 64, as shown in FIG. 1. The ear panels 62 and 64 preferably encircle part of the waist of the wearer when the diaper 20 is fitted to the wearer. When the diaper is fitted to the wearer in the conventional configuration, the ear panels 62 and 64 extend from the rear waist region 44 of the diaper 20 around the wearer's hips to the front waist region 46 of the diaper 20 where the ear panels 62 and 64 are fastened forming the diaper's waist closure. When the diaper 20 is used as a pull-on, the ear panels 62 and 64 are fastened as described above to form a pant-like article, as shown in FIG. 3. To fit the pull-on onto the wearer, the wearer's legs are passed through the leg openings and the article is pulled up into position such that the waist feature(s) 34 and the ear panels 62 and 64 fit snugly about the hips and waist of the wearer.

Each ear panel is preferably disposed adjacent one of the longitudinal edges 50 of the containment assembly 22, preferably in at least a portion of the rear waist region 44. While it is not necessary that the pair of ear panels be identical, as shown in FIG. 1, they are preferably mirror images of one another. The ear panel(s) 62 and 64 may comprise portions of other elements of the absorbent article or may be separate elements joined with the containment assembly 22. Each of the ear panels 62 and 64 have a proximal edge, a distal edge, an inner surface, and an outer surface. For example, the first ear panel 62 has a proximal edge 66 disposed adjacent one of the longitudinal edges 50 of the containment assembly 22 in the rear waist region 44 of the diaper 20 and a distal edge 68 spaced laterally outwardly from the proximal edge 66. The inner surface of each ear panel 62 and 64 is designated 67 and the outer surface of each ear panel is designated 69. As shown in FIG. 1, the outer surface 69 of each ear panel is that surface which faces away from the wearer when the diaper is being worn and generally corresponds to the garment facing surface 40 of the containment assembly 22. As shown in FIG. 1, the inner surface 67 of each ear panel is that surface which faces the wearer when the diaper 20 is being worn and generally corresponds to the body facing surface 42 of the containment assembly.

In a preferred embodiment of the present invention, the ear panels 62 and 64 are at least partially elastomeric or elastically extensible in the lateral direction to provide the necessary stretch characteristics to work effectively as a pull-on article and fit a wide range of user sizes. (The "lateral direction" is defined as the direction parallel to the transverse centerline 102 of the diaper.) Elastomeric ear panels also provide more effective application of the diaper since even if the diaperer fits the diaper to the wearer asymmetrically, the diaper may self adjust during wear to attain an improved fit. Further, elastically extensible ear panels provide improved dynamic fit about the waist of the wearer, reducing the possibility of sagging or gapping, and sustaining the fit of the diaper throughout the time of wear.

It has been found that in order for the diaper 20 to work effectively as a pull-on or as a conventional diaper capable of fitting a wide range of wearers that the ear panels 62 and 64 in conjunction with the waist feature(s) 34 should provide sustaining forces within a definite range at certain waist hoop circumferences. (As used herein, the term "sustaining forces" refers to the inwardly directed forces that hold the diaper against the waist and hips of the wearer so as to reduce sagging or gapping during use. The sustaining force will often be less than the force needed to stretch the material to the length in which the sustaining force is measured. The term "waist hoop circumference" and "hip hoop circumference" refers to the circumference of the waist of the diaper when it is fully constructed into a pant-like article, either before being pulled onto the wearer or after being fitted to the wearer in the conventional configuration.) In preferred embodiments, the waist hoop circumference of the diaper 20 in a relaxed state (i.e. having no tension applied) is smaller than the waist of the smallest wearer in the size range. Likewise, the waist hoop circumference of the diaper 20 in a fully stretched condition is preferably larger than the circumference of the waist of the largest expected wearer in the particular size range. (As used herein, the term "fully stretched" means that the waist hoop of the diaper has been stretched to its elastic limit, at which point any further force applied would deform, destroy or otherwise alter the structure of at least a portion of the material. Alternatively, the term "fully stretched" may refer to the waist of the diaper when the side panels have been stretched to a degree that any further stretching would be unacceptable for such a product, generally greater than 3500 grams.) This ensures that the diaper will properly fit all wearers in any size range and will function properly as a pull-on/off article.

Preferably, the waist hoop circumference of the diaper 20 in a relaxed state is between about 280 mm and about 360 mm (These numbers generally correspond to medium to large babies.). In a fully stretched condition, the waist hoop circumference is between about 550 mm and about 600 mm. The sustaining force resulting from the waist hoop being fully stretched is preferably less than about 2000 grams. In preferred embodiments, as shown in below, the sustaining force should be greater than about 250 g when the waist hoop is stretched to a circumference of between about 340 mm and about 390 mm. (This range of waist hoop circumferences generally represents the waist size of medium wearers, about 6 Kg to about 10 Kg.) Further, in preferred embodiments, the sustaining forces should be less than about 2000 g when the waist hoop is stretched to a circumference of between about 510 mm and about 560 mm. (This range represents generally the bigger waist circumference of medium to large babies.) For adult wearers, the sustaining forces should preferably be between less than about 3000 g when the hip hoop circumference is stretched to between about 1000 mm and about 1450 mm.

The following chart includes information relating to preferred embodiments of the absorbent article of the present invention.

"recovery force" is used to denote the load which can be obtained from the recovery or relaxation curve of a stress/strain graph.) Further, it is preferred that each ear panel elastomeric portion also be capable of extending between about 150% and about 300% when a force of less than about 3000 grams is applied. (The percentages described above are calculated by subtracting the relaxed state length from the extended length, dividing that number by the relaxed state length and multiplying the result by 100%.) In preferred embodiments, each ear panel has an elastomeric portion having a relaxed state length which is defined as the length of the elastomeric portion of the ear panel measured along an axis that is generally parallel to the direction of forces to be applied to extend the ear panel. Once extended, the ear panel elastomeric portion has an extended length which is defined as the length of the ear panel elastomeric portion measured along an axis that is generally parallel to the direction of the forces applied to extend the ear panel. When the extension force is released, the panels are allowed to recover, or contract. In preferred embodiments, each side panel elastomeric portion exhibits a recovery force of greater than about 250 grams when each panel is extended between about 30% and about 70%.

The ear panels 62 and 64 may take on a number of different sizes, shapes, configurations and materials. The exact length, width and thickness of the ear panels 62 and 64 may vary depending on the intended user. The ear panels 62 and 64 may comprise a portion of the material making up one or more of the diaper elements, including the topsheet 24, the backsheet 26, or the waist feature 34. Alternatively, the ear panels may comprise a separate element or a plurality of elements joined to the diaper 20. In one preferred embodiment, the ear panels 62 and 64 comprise multi-directional extensible side panels. Such side panels are described in detail in copending U.S. patent application Ser. No. 08/155/048 entitled "Absorbent Article With Multi-Directional Extensible Side Panels", filed on Nov. 19, 1993 in the names of Miguel Robles et al., which is hereby incorporated by reference herein. The ear panels 62 and 64 may also be extensions of a belt-like element 77 which includes both ear panels 62 and 64. The belt-like element 77 preferably extends across the containment assembly 22 of the diaper 20 and laterally outwardly therefrom to form the ear panels 62 and 64. The belt-like element 77 may be integral with other elements of the diaper or may be a separate element attached thereto. If the belt-like element 77 or the ear panels

| Approximate size or build of wearer | Minimum waist (on babies) or hip (on adults) circumference of wearer | Maximum waist or hip circumference of wearer | Minimum waist or hip circumference of absorbent article in its relaxed state | Maximum waist or hip circumference of absorbent article in its fully stretched state when a force of less than about 2000 g is applied (for babies) or less than about 3000 g is applied (for adults) |
|---|---|---|---|---|
| Medium to Large Babies | 340-390 mm | 510-560 mm | 280-360 mm | 550-600 mm |
| Extra-Large Babies | 390-410 mm | 600-640 mm | 300-380 mm | 600-700 mm |
| Medium Adults | 690-710 mm | 940-960 mm | 550-600 mm | 1000-1200 mm |
| Large Adults | 890-910 mm | 1190-1240 mm | 700-750 mm | 1350-1450 mm |

Alternatively, the stretch characteristics of the diapers of the present invention can be defined in terms of the amount of extension that the side panels 62 and 64 provide while providing certain recovery forces. (As used herein, the term

62 and 64 are separate elements joined to the diaper 20, they can be joined by any by any means as known in the art. Examples of suitable attachment means include adhesive bonding, heat bonding, pressure bonding, ultrasonic bonding, dynamic mechanical bonding or a combination of any of these means or any other means as are known in the art.

One elastically extensible material that has been found to be especially suitable for use in the ear panels 62 and 64 is a laminate of at least one coverstock layer joined with an elastomeric film. (As used herein, the term "coverstock" refers to any woven or nonwoven materials.) Examples of suitable coverstock materials are hereinbefore discussed with respect to the topsheet 24 and the backsheet 26. Other suitable coverstock materials include nonwovens such as Fiberweb E004203 available from Fiberweb North America of Simpsonville, S.C., and Veratec 7pt., P-8 and P-14 available from Veratec Nonwoven Group of the International Paper Company of Walpole, Wash. Examples of suitable elastomeric films include Clopay 2870, a styrene block copolymer available from the Clopay Corporation of Cincinnati, Ohio, and Exxon 550 available from the Exxon Chemical Company of Lake Zurich, Ill. Examples of suitable synthetic foams for joining between the coverstock layers include: a) crosslinked natural rubber foams preferably having a caliper of approximately 50 mils and a density of approximately 13.3 pounds per cubic foot (0.214 grams per cubic cm), such as is available from Fulflex Inc., of Middletown, R.I., or as available from Ludlow Composites Corporation of Freemont, Ohio and marketed under the tradename Baby Foam; or b) polyurethane foams having a caliper of approximately 80 mils and a density of approximately 2.06 pounds per cubic foot (0.033 grams per cubic cm), such as is available from Bridgestone of Yokohama, Japan and marketed under the tradename Bridgestone SG Polyurethane Foam. Other suitable materials for use as or in the ear panels include structural elastic-like film (SELF) webs, as described above, natural rubber, natural rubber foams, elastomeric scrims, woven or nonwoven elastomeric webs, elastomeric composites such as elastomeric nonwoven laminates, zero strain stretch laminates, prestrained stretch laminates or the like. The above referenced U.S. Pat. No. 5,151,092 issued to Buell et al., on Sep. 29, 1992, describes suitable zero strain stretch laminates and prestrained stretch laminates, and is herein incorporated by reference.

In an alternative embodiment, the side panels 62 and 64 may comprise a laminate including an elastomeric scrim material. In one such preferred embodiment, the ear panels 62 and 64 may comprise a laminate of a scrim laminated between nonwovens, films, scrims, laminates or any combinations thereof. Suitable nonwovens include those mentioned above, as well as the carded polypropylene RMS 66265 available from Veratec Nonwoven Group of the International Paper Company of Walpole, Wash.; and the spunbond polyethylene available from Corovin GmbH of Germany under the trade name COROLIND. A suitable scrim is available from Conwed Plastics under the trade name REBOUND ELASTOMERIC NETTING, having between 2 and 20 strands per inch extending in the machine direction and the cross-direction. In yet another embodiment, the ear panels 62 and 64 may comprise a laminate including a formed film such as X-15301 manufactured by Tredegar Film Products, Inc. of Terre Haute, Ind.

Figure 7:
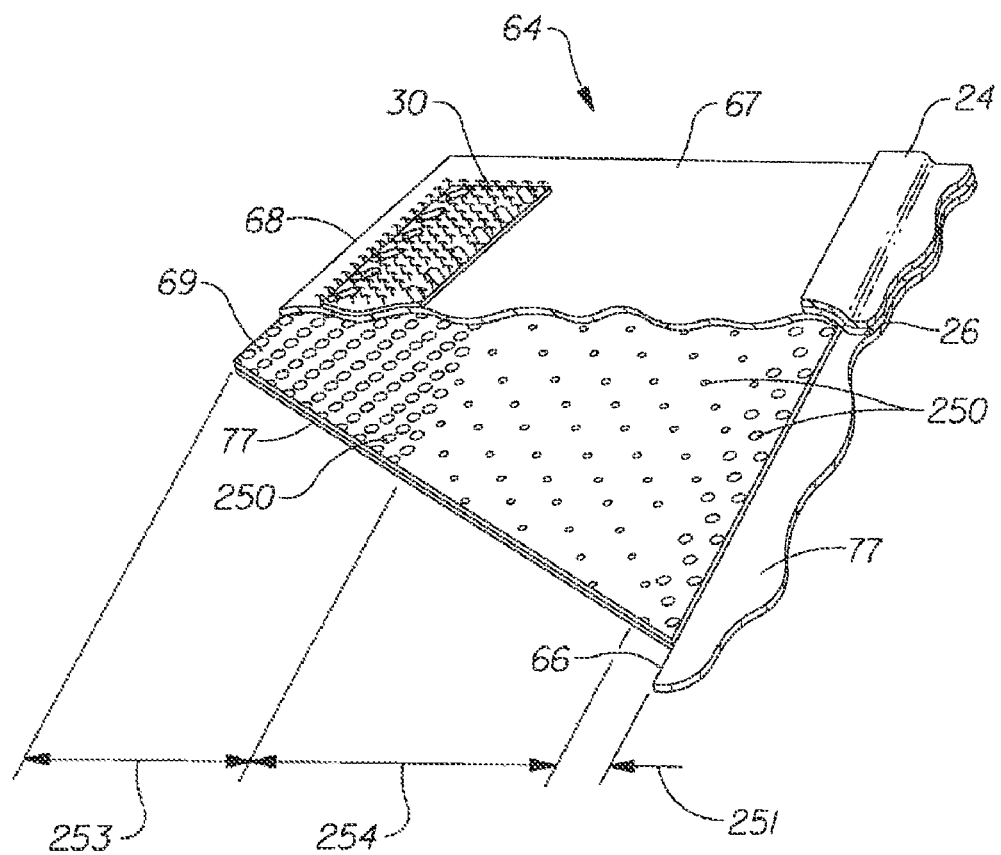
FIG. 7 is a cut away plan view of one embodiment of an ear panel of the present invention comprising differential bonding.

One preferred material for the ear panels has a relatively flat stress-strain curve between 50% and 200% elongation to sustain product fit on the baby and make the diaper relatively easy to apply. One material that works especially well is a laminate made with elastomeric scrim (TN2510) from Conwed Plastics. The laminate typically consists of 3-5 layers, including the scrim. The layers other than the scrim preferably comprise nonwovens, films or apertured films. The laminate may be bonded by any means known in the art for joining layers of a laminate. Examples of suitable bonding means include, but are not limited to, heat, pressure, ultrasound, adhesive, cohesive and coextrusion. In one especially preferred embodiment, the laminate comprises differential bond regions which can be achieved by varying the amount or intensity of the bonding means throughout the laminate. Preferably, the differential bonding creates high bond zones 252 near or at the distal and proximal edges 66 and 68 of the ear panels to prevent creep and provide strength in those zones. (As used herein, the term "high bond zones" refers to those areas of the laminate comprising a relatively high frequency of individual bonds, a relatively greater bonded area or bonds that are relatively stronger than bonds in other areas of the laminate.) The high bond zones, including distal high bond zone 253 and proximal high bond zone 251 (as shown in FIG. 7), may be completely bonded or may comprise a relatively high frequency of bonds or large area of bonding. The high bond zones resist creeping and provide a stronger foundation for any fastening elements that may be joined thereto. The high bond zones also provide a stronger region for joining the side panels to the containment assembly 22 if the side panels are separate elements. Further, the laminate may comprise low bond zones 254, such as central low bond zone 255, as shown in FIG. 7, generally disposed between the high bond zones 251 and 253, and generally in the center of the ear panels. (As used herein, the term "low bond zones" refers to portions of the laminate comprising a relatively lower frequency of individual bonds, a relatively lesser bonded area or bonds that are relatively weaker than bonds in the high bond zones of the laminate.) The low bond zone(s) 254 may provide increased breathability as well as better properties for ring rolling the laminate in those zones. One example of an ear panel comprising differential bonding is shown in FIG. 7, wherein the individual bond sites are designated 250.

The diaper 20 additionally comprises a fastening system 200. The fastening system 200 permits the user to construct and fit the diaper 20 to the wearer in at least two different configurations, a conventional configuration and a pull-on configuration (i.e., the diaper is convertible). The term "conventional configuration" refers to a diaper that is fitted to the wearer by placing the rear waist region 44 of the diaper 20 under the back of the wearer, pulling the front waist region 46 through the legs of the wearer to the wearer's waist and fastening the front waist region 46 to the waist region 44 to form side closures and to complete construction of the diaper 20. A "pull-on" diaper refers to a diaper that is fitted to the wearer by placing the wearer's legs through the leg hole openings and pulling the fully constructed diaper up over the wearer's hips like pants. In either case, the diaper 20 can be removed by pulling the diaper down in its fully constructed configuration or by opening the closures formed by the fastening system 200.

The fastening system 200 may comprise any attachment means known in the art including pressure sensitive adhesives, cohesive materials, mechanical fasteners such as hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu and Robertson on May 5, 1987. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846, 815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

In a preferred embodiment of the present invention, the fastening system 200 comprises hook and loop type fasteners. As used herein, the term "hook and loop type fasteners" refers to fastening means comprising a "hook" component (hereinafter referred to as an "engaging component") and a complementary loop component (hereinafter referred to as a "landing component"). The term "hook" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary landing component.

One embodiment of the present invention comprises an engaging component 202 including a hook fastening material preferably having a base 208 and a plurality of engaging elements 206 extending from the base 208. The hook fastening material is intended to engage fibrous elements of a loop fastening material so as to provide a secure fastening device. Thus, the hook fastening material may be manufactured from a wide range of materials. Further, the engaging elements 206 may have any shape such as hooks, "T's", "mushrooms" or any other shape as are well known in the art. Suitable materials include nylon, polyester, polypropylene, or any combination of these materials. Examples of preferred hook fastening materials are available from Aplix Inc. of Charlotte, N.C. under the trade designation 960, 957 and 942. Other preferred hook fastening materials are available from the Minnesota Mining and Manufacturing Company of St. Paul, Minn. under the trade designations CS200, CS300, MC5 and MC6. Yet another preferred hook fastening material is described in U.S. Pat. No. 5,058,247 entitled "Mechanical Fastening Prong" issued to Thomas Oct. 22, 1991, which is incorporated herein by reference.

Figure 8A:
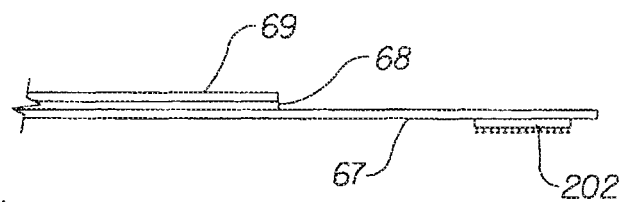
FIGS. 8A-D are partial views of alternative embodiments of an ear panel and structure to which the engaging components of the present invention may be joined.
Figure 8B:
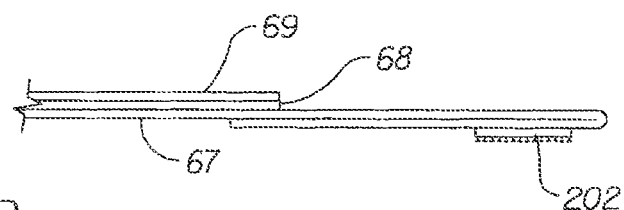
Figure 8C:
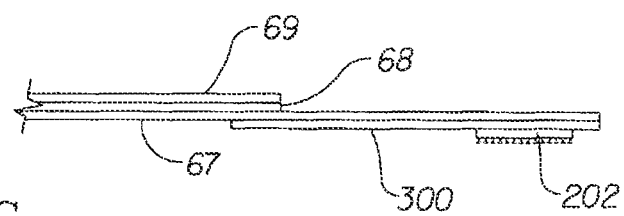
Figure 8D:
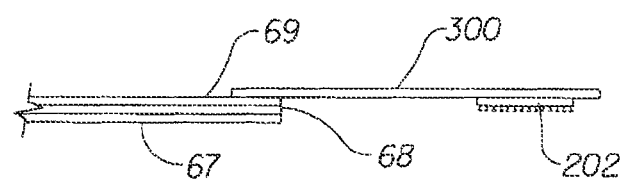

The engaging components 202 may be joined to the absorbent article by any suitable means. They may be directly joined with any portion of the ear panels 62 and 64, such as the material comprising the inner surface of the ear panel 67, or the material comprising the outer surface of the panel 69, or mounted on some intermediate member, such as a tape tab or other tab member. Examples of different configuration for mounting the engaging component 202 to the ear panels 62 and 64 are shown in FIGS. 8A-D. FIG. 8A shows the engaging component 202 joined with a single layer of the material comprising the inner surface of the ear panel 67 extending outwardly from the distal edge 68 of the ear panel 64. FIG. 8B shows the engaging component 202 joined with the material comprising the inner surface of the ear panel 67 extending outwardly from the distal edge 68 of the ear panel 64 which is folded over to create at least two layers. FIG. 8C shows the engaging component 202 joined with a separate material 300 joined with the material comprising the inner surface of the ear panel 67 extending outwardly from the distal edge 68 of the ear panel 64, forming at least two layers. FIG. 8D shows the engaging component 202 joined with a single layer of a separate material 300 joined with the material comprising the outer surface of the ear panel 69, the separate material extending outwardly from the distal edge 68 of the ear panel 64. The tab or separate material 300 may be of any shape or size and may comprise any suitable materials, including single materials or laminates. Further, the tab or separate material 300 may have stretch properties if desirable. Examples of materials which could be used as an intermediate tab include films, wovens, and nonwovens, and the like, or any combination thereof. The tab or the separate material 300 may be joined to ear panel by any means known in the art, including, but not limited to heat, pressure, ultrasound, adhesive, cohesive or any combination of these or other bonding means.

In any of the above-described configurations, it may be desirable to limit the amount of extensibility of the material to which the engaging component 202 is joined. This is due to the possibility that joining the engaging component 202 to an extensible member may result in the engaging elements 206 and/or the base 208 being separated when a force is applied, thus reducing their fastening performance. One way to reduce the extensibility of the material to which the engaging component 202 is joined is to mechanically bond the substrate such that it loses most of its extension properties and becomes relatively inextensible. Alternatively, coatings may be applied to the substrate or materials may be chosen which are relatively inextensible. (As used herein, the term "inextensible" generally refers to materials which elongate less than 10% when a force of greater than 150 grams/inch is applied and which elongate less than 20% when a force of greater than 450 grams/inch is applied.)

The engaging component 202 may be an integral part of the tab or the ear panel, or may be a separate member joined with the tab or ear panel. Preferred means for joining the engaging component 202 to either the tab or the ear include, but are not limited to adhesives, cohesives, heat, pressure, ultrasound or any combination of these or other known bonding means. For example, the hook member may be joined to the tab member or the ear panel with an adhesive as well as a mechanical bond. Mechanical bonding, or fusion of some form may be used alone, or in combination with other bonding means. (The term "mechanical bond" as used herein, refers to bonds formed by means of pressure, ultrasound, heat, laser energy or any form of energy input which mechanically joins the elements.) In an especially preferred embodiment an adhesive bond is used to join the hook member to the absorbent article, supplemented by a mechanical bond.

Figure 6A:
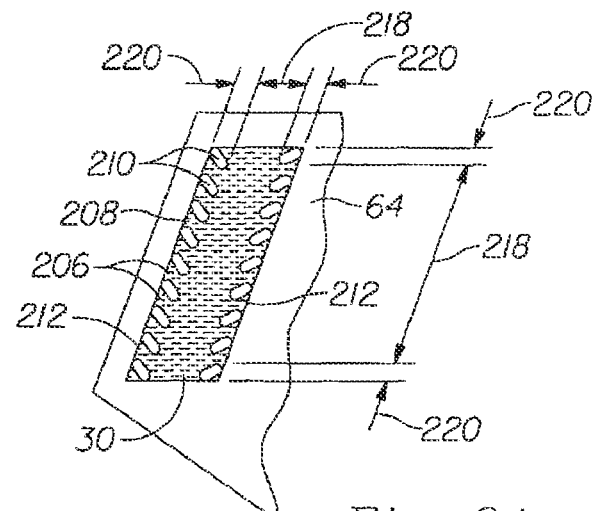
FIGS. 6A-C each show an embodiment of a hook member having a different mechanical bonding pattern.
Figure 6B:
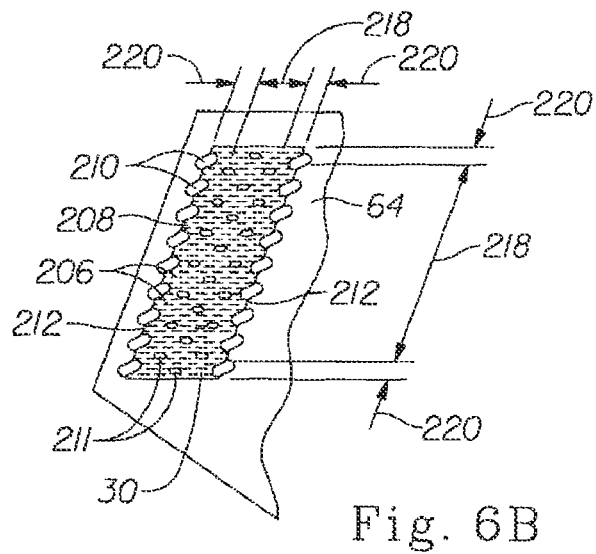
Figure 6C:
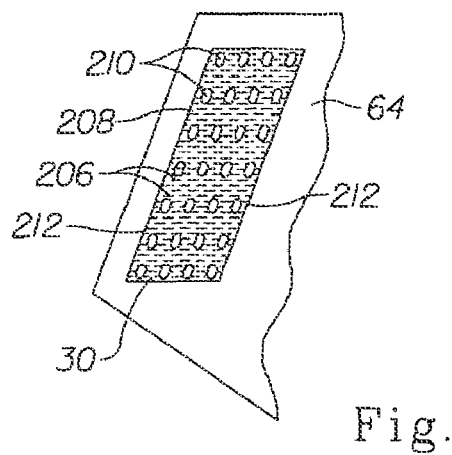

It has been found that if a mechanical bond is used to join the engaging component 202 to an element of the absorbent article, alone or in combination with other bonding means, the mechanical bond pattern may affect the strength of the bond between the engaging component 202 and the element to which it is joined, as well as the fastening characteristics of the engaging component 202. Mechanical bonding typically damages at least some of the engaging elements 206 of the engaging component 202, causing some change in the fastening performance of the component. Thus, it is preferred that a mechanical bond pattern is chosen that securely bonds the engaging component 202 to the absorbent article without damaging too many of the engaging elements 206. Suitable results can be achieved by mechanically bonding the engaging component at predetermined locations along at least its longitudinal outer edges 212 in at least its outer region 220. In especially preferred embodiments, the bonding pattern includes bonds at or near each corner of the engaging component 202, as shown in FIGS. 6A and B. The central region 218 of the engaging component 202 is preferably generally unaffected by the edge mechanical bonds 210. Examples of acceptable and preferred bond patterns are shown in FIGS. 6A-C. The bonding patterns shown in FIGS. 6A and B are particularly effective in securely joining the engaging component 202 with the element to which it is being bonded while minimizing the impact of the center mechanical bonds 211 on the engaging elements 206, and thus, the engaging component's overall fastening performance. This type of bonding and fastening performance is important for products such as the diaper 20 of the claimed invention in which the fastening elements control the majority of the ear panel when in use. The implication of this control of the ear panel is that shear and peel forces provided by the movements of the wearer tend to separate the engaging component 202 from the ear panel or tab to which it is joined. Such forces may also disengage the engaging component 202 from its complementary landing component 204.

The advantages of the bonding patterns shown in FIGS. 6A and B are thought to be due to the relatively large, strong edge bonds 210 provided in at least a portion of the outer region 220 of the engaging component 202 along the longitudinal outer edges 212. The patterns shown in FIGS. 6A and B also leave the majority of the engaging elements 206 intact in at least the central region 218 of the engaging component 202 such that engaging component's fastening performance is not significantly jeopardized. The central region 218 of the engaging component 202 comprises that area of the engaging component which is surrounded by the outer region 220 including the longitudinal outer edges 212 and the lateral outer edges 214 and 216. In preferred embodiments, the central region 218 comprises relatively smaller bonds, such as center bonds 211 as shown in FIG. 6B, or alternatively a smaller number of bonds that are similar in size to the edge bonds 210. In fact, it may be desirable to chose a bond pattern that does not comprise any bonds in the central region 218. In preferred embodiments comprising center bonds 211 which are generally smaller in area than the edge bonds 210, the center bonds 211 are preferably less than about 66%, and more preferably less than about 25% of the size of the edge bonds 210. (As used herein, the term "area" refers to the plan view area of each individual bond as viewed from above.) The center bonds 211 may be used to help ensure that the central region 218 of the engaging component 202 will not be easily unjoined from the underlying structure.

The edge mechanical bonds 210 of the present invention may be of any suitable size, shape density or configuration. However, in preferred embodiments, as shown in FIGS. 6A and B, the edge mechanical bonds 210 are generally elliptical in shape and are oriented such that their major axis is nonparallel to either the longitudinal outer edges 212 or the lateral outer edges 214 and 216 of the engaging component 202. It is preferred that the edge mechanical bonds 210 are generally similar in shape and orientation to one another, creating a bonding pattern that extends from one lateral outer edge to the other, generally along each of the longitudinal outer edges 212. (However, embodiments are contemplated wherein the edge mechanical bonds 210 extend along only one longitudinal outer edge 212 of each engaging component 202 or the edge mechanical bonds 210 may not extend along the entire longitudinal edge 212. In such embodiments it is preferred that the laterally inboard outer region 220 comprises the edge mechanical bond(s) 210.) The bonding pattern preferably comprises a series of edge mechanical bonds 210 in a generally repetitive pattern. However, it is contemplated that the edge mechanical bonds 210 may comprise a single bond that extends generally from one lateral outer edge to the other. It is preferred that at least a portion of an edge mechanical bond 210 is located at or near each of the corners of the engaging component 202. Further, it may be preferred that at least a portion of the edge mechanical bond(s) 210 overlap at least a portion of the structure generally underlying the engaging component 202, as shown in FIG. 6B. The pattern of the edge mechanical bonds 210 may be the same along each longitudinal outer edge 212 and/or lateral outer edge 214 or 216, or may be different.

In preferred embodiments including center mechanical bonds 211, it is preferred that the center mechanical bonds 211 are relatively smaller than the edge mechanical bonds 210, or are less densely concentrated in at least the central region 218. The center mechanical bonds 211 of the present invention may be of any suitable size, shape density or configuration. However, in preferred embodiments, as shown in FIG. 6B, the center mechanical bonds are generally elliptical in shape. It is preferred that the center mechanical bonds 211 are generally similar in shape and size to one another, creating a generally repetitive bonding pattern that extends throughout the central region 218. (Embodiments are contemplated wherein the center mechanical bonds 211 extend at least partially into the outer region 220.) In preferred embodiments, the center mechanical bonds 211 should occupy less than about 20%, more preferably less than about 10%, and most preferably less than about 7% of the area of the central region 220. This will assure that the center mechanical bonds 211 do not damage too many engaging elements 206, and thus, will not significantly reduce the effectiveness of the engaging component 202 or the overall fastening system 200.

The percentage of area occupied by the bonds is preferably measured by examining a representative sample of the engaging component 202 under a microscope. The sample is viewed under the microscope from directly above the side from which the engaging elements 206 extend. The plan view area of each of the bonds 210 or 211 is measured. The sum of the areas of the bonds 210 or 211 is divided by the area of the sample. The result is expressed as a percentage. This is the percentage of area occupied by the bonds 210 or 211.

The landing component 204 preferably comprises a fastening element engageable with the engaging component 202. Thus, the landing component 204 may be manufactured from a wide range of materials and configurations capable of securely engaging the engaging component 202. For example, the landing component 204 may comprise identical complementary elements or distinct complementary elements. As used herein, the term "identical complementary elements" is used to define mechanical fastening systems wherein the engaging elements of the engaging component 202 and the landing component 204 comprise the same configuration or structure. Examples of such systems are described in Brown et al. U.S. Pat. No. 4,322,875 entitled "Two Strip Materials Used For Forming Fasteners" issued on Apr. 16, 1982 and Kellenberger et al. U.S. Pat. No. 4,701,179 entitled "Fixed Position Fasteners For Disposable Absorbent Garments" issued on Oct. 20, 1987. The term "distinct complementary elements" is used herein to designate a system wherein the engaging component 202 is different from the landing component 204 but is engageable therewith.

In one preferred embodiment, the landing component 204 comprises a plurality of fiber elements, such as a loop fastening material, that engage the engaging elements 206 of the engaging component 202. The loop fastening material may be manufactured from a wide range of materials to provide fiber elements, preferably loops. Suitable materials include woven materials, nonwovens, nylons, polyesters, polypropylenes, or any other known loop fastening materials or combination of these materials. One suitable loop fastening material is a nonwoven available from Minnesota Mining and Manufacturing Company, St. Paul, Minn. under the trade designation EBL. A preferred loop fastening material comprises a number of shaped engaging elements projecting from a woven backing such as the commercially available material designated Guilford 18904 available from Guilford Mills of Greensboro, N.C. Other suitable landing components are available from the Minnesota Mining and Manufacturing Company of St. Paul, Minn. under the trade designation KLT. An inexpensive loop fastening material and a method of making the same is described in U.S. Pat. No. 5,032,122, entitled "Loop Fastening Material For Fastening Device and Method of Making Same" issued to Noel et al., Jul. 16, 1991, which application is incorporated herein by reference. Another suitable landing component material is described in U.S. Pat. No. 5,326,612 entitled "Nonwoven Female Component for Refastenable Fastening Device and Method of Making the Same" issued to David J. K. Goulait on Jul. 5, 1994, which is hereby incorporated by reference herein. Yet other suitable landing components are described in co-pending U.S. patent application Ser. No. 08/254,814 entitled "Nonwoven Female Component For Refastenable Fastening Device and Method of Making the Same" filed Jun. 6, 1994 in the names of Patrick Jay Allen et al.; U.S. patent Ser. No. 08/287,571 entitled "Nonwoven Female Component For Refastenable Fastening Device" filed Aug. 9, 1994 in the names of Willie F. King et al.; and U.S. patent Ser. No. 08/374,269 entitled "Female Component For Refastenable Fastening Device" filed Jan. 18, 1995 in the names of Carl L. Bergman et al.

The landing component 204 may be joined with the diaper 20 by any means known in the art, including but not limited to adhesives, cohesives, heat, pressure, ultrasound, or any combination thereof. Further, the specific bonding patterns described above with regard to the engaging components 202 may be used to join the landing component(s) 204 to the diaper 20. Preferably, the landing component(s) 204 is joined with the diaper 20 by means of an adhesive bond which may cover any portion of its backing.

The elements of the fastening system 200 may be disposed on either the garment facing surface 40 or the body facing surface 42 of the diaper 20. In a preferred embodiment, however, the fastening elements are disposed on the diaper 20 such that the fasteners do not irritate the wearer's skin. In addition, the fastening elements, including the engaging components 202 and the landing component(s) 204 may either be discrete separate elements affixed to the diaper 20 or unitary elements which are neither divided nor discontinuous with another element of the diaper 20, such as the topsheet 24 or the backsheet 26. It should be noted that the engaging components 202 and the landing component(s) 204 may be of any shape and size. Further, embodiments are contemplated wherein the engaging components 202, the landing components 204, or both are not continuous, but rather include a number of individual members that provide the requisite fastening characteristics and to allow for the best fit for a broad range of wearers.

In many embodiments of the present invention, most of the waist hoop stress is transmitted through the fastening system 200. (As used herein, the term "waist hoop stress" refers to the forces that are created in throughout the waist regions 44 and 46 of the diaper 20 when the diaper is worn, including the time when the diaper is being fitted to the wearer or being removed.) However, traditional tape tabs and mechanical fasteners are generally insufficient to control the ear panels or unable to withstand the waist hoop stress forces associated with a diaper that is designed to be capable of being pulled on or off, even with supplemental fastening elements. Traditional tape and mechanical fastening systems generally comprise discrete tabs located and oriented to direct only certain waist hoop stress forces to specific predetermined regions. Thus, it is generally preferred that the engaging components 202 comprised in the fastening system 200 of the present invention control a large portion of each ear panel 62 or 64 adjacent the distal edges 68. This relatively large area of control provided by the engaging components 202 (nonlimiting examples of which are shown in FIGS. 1-3) should withstand the waist hoop stress forces normally associated with a diaper that is being worn, or one that is being fitted to the wearer or being removed. Ranges of forces that would be considered to be normally associated with the use of the diaper of the present invention are hereinbefore described with regard to the different waist hoop circumferences.

In preferred embodiments of the present invention, the longitudinal edges 212 of the engaging components 202 may be generally parallel with the longitudinal centerline 100 of the absorbent article, as shown in FIG. 2, or may be at an angle to the longitudinal centerline 100, as shown in FIGS. 1 and 3. Providing the engaging components 202 at an angle to the longitudinal centerline 100 of the absorbent article has at least two benefits. (An alternative to angling the engaging components 202 is to fasten the engaging components 202 to their corresponding landing components 204 at an angle.) When the engaging components 202 are angled, as shown in FIGS. 1 and 3, at least a portion of the longitudinal outboardmost end 214 is laterally inboard of the longitudinal inboardmost end 216. The line parallel to the laterally inboardmost longitudinal edge 212 is hereinafter referred to as the "closure member major axis A". In this configuration, the engaging components 202 are located such that skin marking on the upper thigh is generally avoided, despite the motions of the wearer. Further, keeping the longitudinal outboardmost ends 214 separated laterally helps keep the chassis 22 to maintain proper fit during use. Also, with this approach, the entire fastener can fit into and not straddle the wearer's leg crease, as angled tapes do which risks skin marking.

Figure 9A:
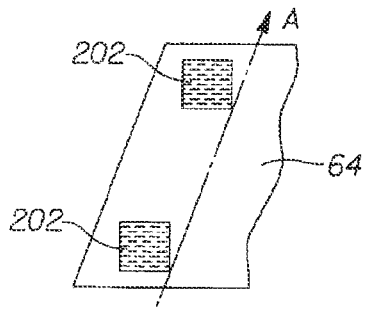
FIGS. 9A-D are partial views of alternative embodiments of an ear panel and the engaging components joined thereto.
Figure 9B:
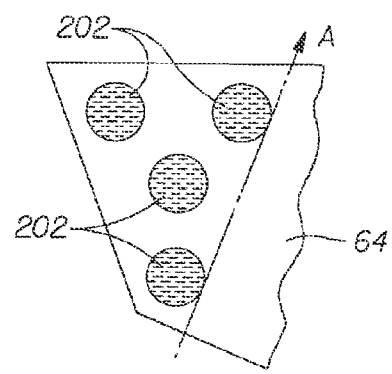
Figure 9C:
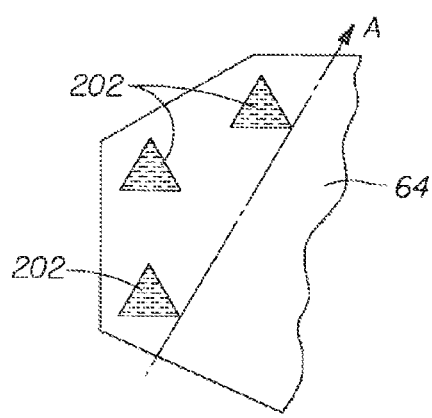
Figure 9D:
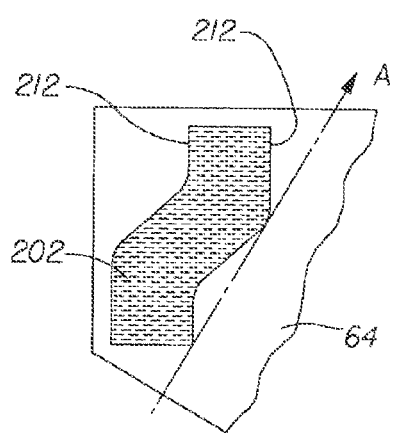

Alternatively, as shown in FIGS. 9A-D, the first and second closure members, 30 and 31, may each comprise more than one engaging component. Further, the engaging components 202 may be similar or different in size and/or shape. In preferred embodiments, the multiple engaging components should be arranged to gain the benefits described above with regard to the single angled engaging components 202. Thus, the "closure member major axis A" in multi-component embodiments is drawn between the laterally inboardmost points of each engaging component 202. The closure member major axis A will be nonparallel to the longitudinal centerline 100 of the absorbent article. In preferred embodiments, the closure member major axis A will converge toward the longitudinal centerline 100 as it moves away from the lateral centerline 102 of the absorbent article toward the end edge 52 in the rear waist region 44 (when in a flat out configuration). In yet another embodiment, as shown in FIG. 9D, the engaging component 202 may be a single member with curved or nonuniform longitudinal outer edges 212. In such embodiments, it is preferred that the closure member major axis A be drawn between the two laterally inboard most points of the laterally inboardmost longitudinal outer edge 212. Preferably, as described above, the closure member major axis A will converge toward the longitudinal centerline as it moves away from the lateral centerline 102 of the absorbent article toward the end edge 52 in the rear waist region 44 (when in a flat out configuration).

Figure 2A:
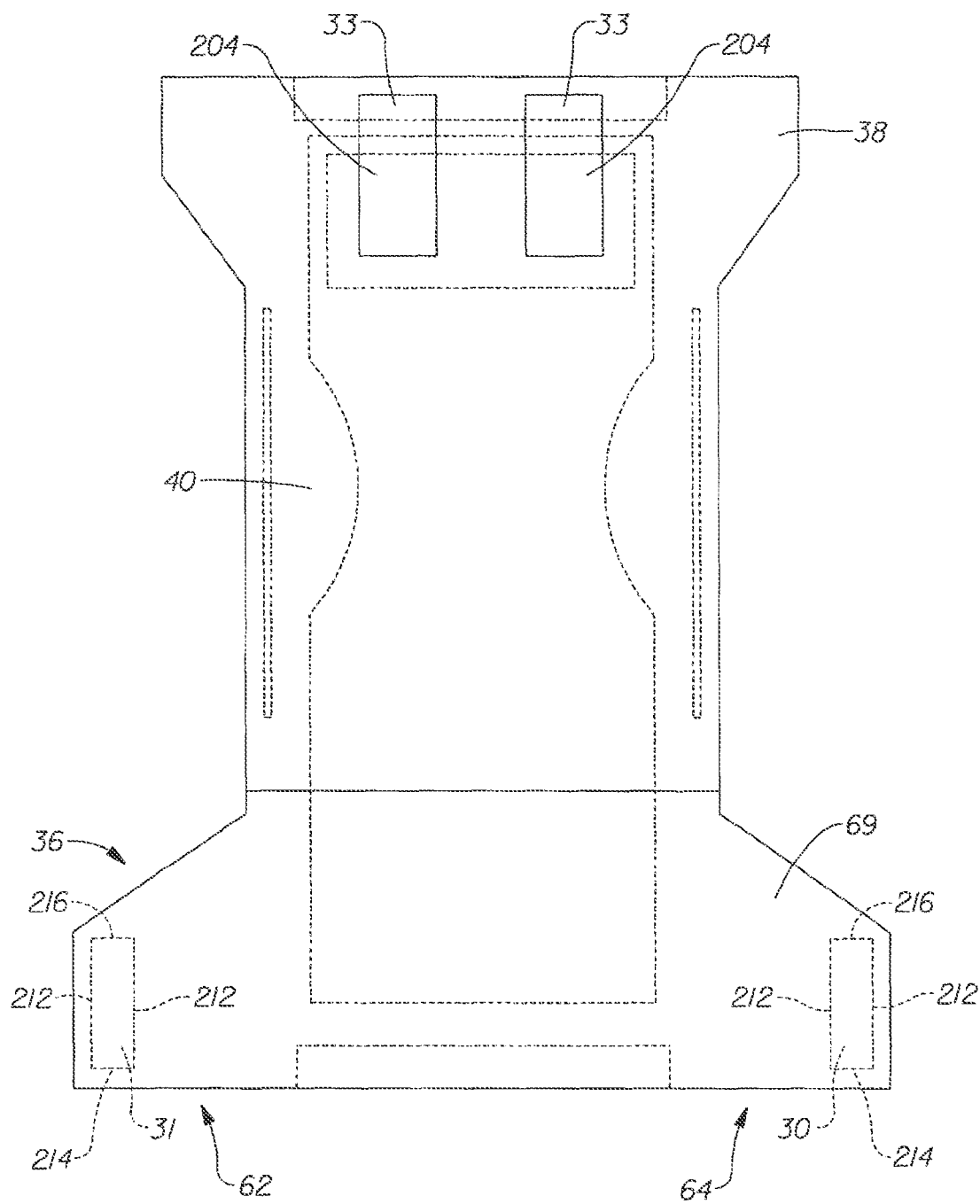
FIG. 2A is a plan view of an alternative embodiment of the present invention having portions cut away to reveal underlying structure, the outer surface of the diaper is facing the viewer.
Figure 2B:
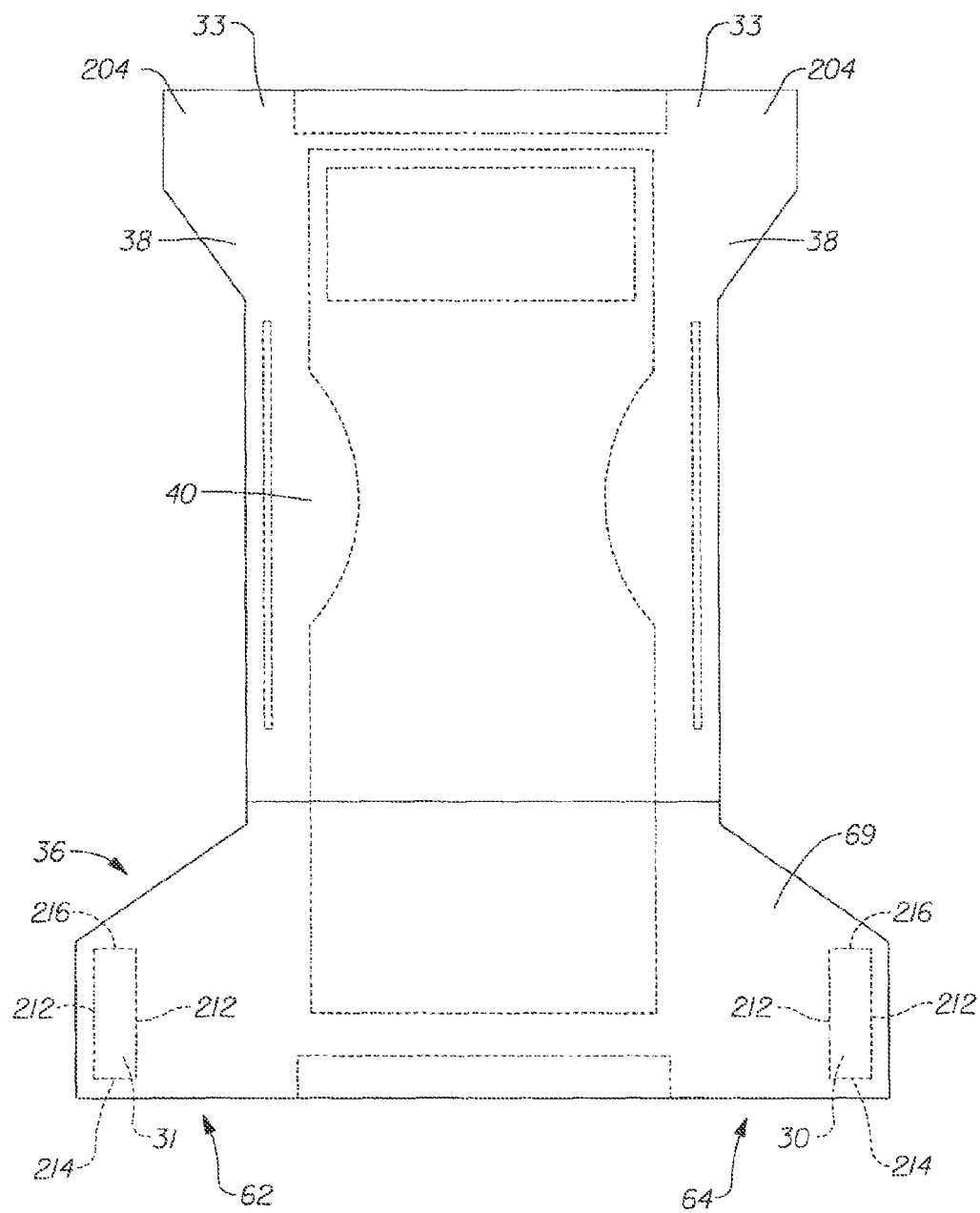
FIG. 2B is a plan view of another embodiment of the present invention with the outer surface of the diaper is facing the viewer.

As shown in FIGS. 2A and 2B, the fastening system 200 of the present invention preferably comprises a first ear panel closure member 30, a second ear panel closure member 31, and a pair of third closure members 33. The first ear panel closure member 30 preferably comprises an engaging component 202 and is preferably disposed adjacent the first ear panel's distal edge 68 on the inner surface 67. The first ear panel closure member 30 may either be a discrete separate element affixed to the diaper 20 or a unitary piece of material that is neither divided nor discontinuous with an element of the diaper 20. When the diaper 20 is constructed, the second ear panel closure member 31 engages one of the third closure members 33 to fasten the rear waist region 44 to the front waist region 46.

The second ear panel closure member 31 preferably comprises an engaging component 202 and is preferably disposed adjacent the second ear panel's distal edge 68, on the inner surface 67. The second ear panel closure member 31 may either be a discrete separate element affixed to the diaper 20 or a unitary piece of material that is neither divided nor discontinuous with an element of the diaper 20 such as the topsheet 24. When the diaper 20 is constructed, the second ear panel closure member 31 engages one of the third closure members 33 to fasten the rear waist region 44 to the front waist region 46. (It should be noted that either or both of the ear panel closure members 30 or 31 may be disposed on the outer surface 69 of the ear panels so long as at least a portion of the fastening surface of the closure member faces the same direction as the inner surface 67 of the ear panel(s) 62 or 64. As used herein, the term "fastening surface" refers to the surface of a fastening element that is engageable with the fastening surface of another fastening element or any other surface of any element of the diaper.)

The third closure member 33 preferably comprises at least one landing component 204 disposed in the front waist region 46. The third closure member 33 is preferably a separate element disposed on the garment facing surface 40 of the diaper 20 such that the fastening surface faces the wearer. However, embodiments are contemplated wherein the third closure member 33 is unitary with elements making up the front waist region 46 or other elements of the diaper 20, such as the topsheet 24. In one preferred embodiment, the third closure member 33 comprises at least two separate discrete patches or areas in the first waist region 46. Examples of preferred configurations of the present invention comprising two landing components 204 are shown in FIGS. 2 and 3. Such configurations can help to ensure a proper waist circumference and proper tensioning for the diaper to perform as either a conventional diaper or a pull-on. Another means for assuring proper tensioning and fit can be provided by the use of a single third closure member 33 with indicia indicating the proper positioning of each of the ear panel closure members 30 and 31 thereon. (Discrete individual landing components 204, as shown in FIGS. 2 and 3, may also be provided with indicia thereon.)

The third closure member(s) 33 may take on any suitable shape or size. In one preferred embodiment, as shown in FIG. 3, the third closure 33 member comprises two distinct landing components which are generally in the shape of parallelograms. In such embodiments, it may be desirable for the landing components 204 comprised in the third closure member 33 to be configured such that their major axis is at an angle to both the longitudinal centerline 100 and the lateral centerline 102 of the absorbent article. It is preferred that the major axis of the landing components 204 be angled laterally outwardly as it extends away from the lateral centerline 102 towards the end edge 52 in the front waist region 46. It is also preferred that the landing components 204 of the third closure member 33 be configured so as to correspond to the angle of the first and second closure members 30 and 31 when the diaper is fastened about the wearer. This ensures that a sufficient portion of each closure member engages with each corresponding landing component. (Embodiments are contemplated, however, wherein the first and second closure members 30 and 31 are not necessarily configured such that they correspond to the angle of the landing component(s) 204. In such cases, the diaperer is left with the flexibility to fasten the fastening system 200 such that the engaging components 202 completely overlap the landing component(s) 204 or not.)

The present invention also preferably comprises a reinforcing member 75. The reinforcing member 75 is preferably disposed in the first waist region 46 for the purpose of adding strength to the diaper 20 in the first waist region 46. In a preferred embodiment, as shown in FIG. 1, the reinforcing member 75 is preferably disposed at least partially coincident with the third closure member(s) 33. (As used herein, the term "coincident" refers to elements of the diaper that in some way touch or overlap. It should be noted, however that the term is not limited to those elements that are in direct contact with one another. Thus, embodiments are contemplated wherein the coincident elements are separated by one or more layers between the elements.) The reinforcing member 75 may help prevent the backsheet 26 of the diaper from tearing or deforming when the elements of the fastening system 200 are disengaged. (As used herein, the term "disengaged" refers to the fastening system 200 elements when they are not in contact with each other.) Accordingly, the reinforcing member 75 may help to ensure that the fastening system 200 maintains its ability to be refastened or used more than once, and preferably many times. The reinforcing member 75 may also act to help prevent the first waist region 46 from collapsing or rolling over when the diaper is being worn, thus, ensuring a better fit throughout the duration of use.

The reinforcing member 75 can be a separate member or members joined with the diaper 20 or an integral part of one or more of the elements of the diaper 20 in at least the first waist region 46. Further, the reinforcing member 75 may take on any size or shape and may be disposed on the inner or outer surface of the backsheet 26, on the inner or outer surface of the topsheet 24, or joined to any other element of the diaper 20 in at least the first waist region 46. The reinforcing member 75 may comprise any materials that will provide the reinforcing characteristics desired by the user, including, but not limited to, woven material, nonwoven material, films, foams, glues, coatings, mechanical or chemical alterations of any element(s) of the diaper, or any combination of the above.

The diaper 20 is may be applied to the wearer in a conventional configuration. To do so, the rear waist region 44 is preferably placed under the wearer's back. The remainder of the diaper 20 is preferably then drawn between the wearer's legs such that the other waist region, preferably the front waist region 46, is positioned across the front of the wearer. The diaperer preferably then grasps the first ear panel 62 or the second ear panel 64, or both and wraps them around the waist of the wearer. The diaperer then engages the first closure member 30 disposed on the inner surface 67 of the first ear panel 62 and the second ear panel closure member 31 disposed on the inner surface 67 of the second ear panel 64 with the third closure member 33 disposed on the garment facing surface 40 of the containment assembly 22 in the front waist region 46. This forms a waist closure on each side of the wearer and completes the construction of the diaper in a conventional configuration.

Alternatively, the diaper may be fitted to the wearer in a pull-on, or pant configuration. The diaper may be constructed generally as stated above before the diaper is placed on the wearer. Accordingly, the diaperer engages the first closure member 30 disposed on the inner surface 67 of the first ear panel 62 and the second ear panel closure member 31 disposed on the inner surface 67 of the second ear panel 64 with the third closure member 33 disposed on the garment facing surface 40 of the containment assembly 22 in the front waist region 46. This forms a pant-like article having a waist hoop and a pair of leg openings. In this configuration, the wearer's legs are directed through the leg openings. Once the wearer's legs are through the leg openings, the diaper can then pull the waist hoop of the diaper up over the wearer's hips such that the waist hoop encircles the waist of the wearer. (It should be noted that the wearer may be the diaperer in some cases, especially when the wearer is a child in the toilet training stage or when the wearer is an adult.)

Of course, the diaper of the present invention may be fitted to the wearer in any other suitable manner, including a combination of the steps described above with regard to the conventional and pull on embodiments. In any configuration, the refastenable fastening system 200 of the present invention provides the user with easy access to inspect the diaper 20 for soiling. Further, the fastening system 200 gives the user the option as to how the diaper 20 will be removed. The diaper 20 can be removed by pulling the diaper 20 down and off the wearer without disengaging the elements of the fastening system 200, or by disengaging at least one of the engaging components 202 form its corresponding landing component 204 and removing the diaper 20 from around the wearer's waist.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pull-on pant-like disposable absorbent article having a first waist region, a second waist region, and a crotch region disposed therebetween, a pair of leg openings and a waist opening, the pull-on pant-like disposable absorbent article comprising:
   a containment assembly comprising a topsheet, a backsheet, and a core between the topsheet and the backsheet, said containment assembly having first and second side edges, and first and second end edges;
   a first elastically extensible flap having a proximal portion and a distal portion, a proximal edge and a distal edge, said first elastically extensible flap comprising at least a layer of nonwoven material joined to an elastomeric material, wherein said first elastically extensible flap is a separate element from said containment assembly and wherein the proximal portion of said first elastically extensible flap is joined to the containment assembly in the first waist region via at least one of a mechanical bond and an adhesive such that said proximal edge of said first elastically extensible flap is disposed inboard of said first side edge of said containment assembly and such that said distal edge of said elastically extensible flap is disposed outboard said first side edge of said containment assembly;
   a second elastically extensible flap having a proximal portion and a distal portion, a proximal edge and a distal edge, said second elastically extensible flap comprising at least a layer of nonwoven material joined to an elastomeric material, wherein said second elastically extensible flap is a separate element from said containment assembly and wherein the proximal portion of said second elastically extensible flap is joined to the containment assembly in the first waist region via at least one of a mechanical bond and an adhesive such that said proximal edge of said second elastically extensible flap is disposed inboard of said first side edge of said containment assembly and such that said distal edge of said elastically extensible flap is disposed outboard said second side edge of said containment assembly; and
   a refastenable fastening system, the refastenable fastening system comprising:
      a landing component comprising a plurality of fiber elements, wherein said second waist region comprises said landing component;
      a first engaging component comprising a base and a plurality of engaging elements projecting from said base, wherein said first engaging component is joined to the distal portion of the first elastically extensible flap via at least one of a mechanical bond and an adhesive such that said first engaging component is disposed outboard said first side edge of said containment assembly;
      a second engaging component comprising a base and a plurality of engaging elements projecting from said base, wherein said second engaging component is joined to the distal portion of the second elastically extensible flap via at least one of a mechanical bond and an adhesive such that said second engaging component is disposed outboard said first side edge of said containment assembly;
      wherein the proximal portion of each of the first and second elastically extensible flaps comprises a high bond zone and wherein the first engaging component releasably engages a portion of the landing component and the second engaging component releasably engages a portion of the landing component such that the pant-like disposable absorbent article comprises leg openings and a waist opening and is in a pull-on configuration.

2. The pull-on pant-like disposable absorbent article of claim 1, wherein the first and second elastically extensible flaps each comprise a central portion between the proximal and distal portions and wherein the central portion of each of the first and second elastically extensible flaps comprises a low bond zone.

3. The pull-on pant-like disposable absorbent article of claim 2, wherein the distal portion of each of the first and second elastically extensible flaps comprises a high bond zone.

4. The pull-on pant-like disposable absorbent article of claim 1, wherein the base of the first engaging component is disposed on a body-facing surface of the first elastically extensible flap and wherein the base of the second engaging component is disposed on a body-facing surface of the second elastically extensible flap.

5. The pull-on pant-like disposable absorbent article of claim 4, wherein the base of the first engaging component overlaps with at least a portion of the high bond zone of the distal portion of the first elastically extensible flap and wherein the base of the second engaging component overlaps with at least a portion of the high bond zone of the distal portion of the second elastically extensible flap.

6. The pull-on pant-like disposable absorbent article of claim 3 wherein each of the first and second engaging components comprise a base and a plurality of engaging elements extending from the base and wherein the base of the first engaging component is joined to the first elastically extensible flap such that the base overlaps with the high bond zone of the distal portion of the first elastically extensible flap and wherein the base of the second engaging component is joined to the second elastically extensible flap such that the base overlaps with the high bond zone of the distal portion of the second elastically extensible flap.

7. The pull-on pant-like disposable absorbent article of claim 1 wherein each of the first and second engaging components comprise a base and a plurality of engaging elements extending from the base and wherein the base of the first engaging component is joined to an elastically extensible portion of the first elastically extensible flap and wherein the base of the second engaging component is joined to an elastically extensible portion of second elastically extensible flap.

8. The pull-on pant-like disposable absorbent article of claim 1 wherein each of the first and second elastically extensible flaps comprise a nonwoven material joined to an elastomeric material, wherein each of the first and second engaging components comprise a base and a plurality of engaging elements extending from the base and wherein the base of the first engaging component is joined to the first elastically extensible flap such that the base does not overlap with the elastomeric material of the first elastically extensible flap and the base of the second engaging component is joined to the second elastically extensible flap such that the base does not overlap with the elastomeric material of the second elastically extensible flap.

9. The pull-on pant-like disposable absorbent article of claim 1 wherein each of the first and second elastically extensible flaps comprise an elastomeric material positioned between a first nonwoven material and a second nonwoven material.

10. The pull-on pant-like disposable absorbent article of claim 1 wherein the backsheet comprises a liquid impervious film.

11. The pull-on pant-like disposable absorbent article of claim 10 wherein the proximal portion of the first elastically extensible flap and the proximal portion of the second elastically extensible flap overlap with the backsheet.

12. The pull-on pant-like disposable absorbent article of claim 11 wherein the proximal portion of the first elastically extensible flap and the proximal portion of the second elastically extensible flap overlap with the liquid impervious film of the backsheet.

13. The pull-on pant-like disposable absorbent article of claim 12 wherein the backsheet comprises a nonwoven material joined to the liquid impervious film.

14. The pull-on pant-like disposable absorbent article of claim 13 wherein the backsheet is breathable.

15. The pull-on pant-like disposable absorbent article of claim 1 wherein the fiber elements are made of a material chosen from at least one of a woven material, a nonwoven material, nylon, polyester and polypropylenes.

16. A pull-on pant-like disposable absorbent article having a first waist region, a second waist region, and a crotch region disposed therebetween, a pair of leg openings and a waist opening, the pull-on pant-like disposable absorbent article comprising:
a containment assembly comprising a topsheet, a backsheet, and a core between the topsheet and the backsheet, said containment assembly having first and second side edges, and first and second end edges;
a first elastically extensible flap having a proximal portion and a distal portion, a proximal edge and a distal edge, said first elastically extensible flap comprising at least a layer of nonwoven material joined to an elastomeric material, wherein said first elastically extensible flap is a separate element from said containment assembly and wherein the proximal portion of said first elastically extensible flap is joined to the containment assembly in the first waist region via at least one of a mechanical bond and an adhesive such that said proximal edge of said first elastically extensible flap is disposed inboard of said first side edge of said containment assembly and such that said distal edge of said elastically extensible flap is disposed outboard said first side edge of said containment assembly;
a second elastically extensible flap having a proximal portion and a distal portion, a proximal edge and a distal edge, said second elastically extensible flap comprising at least a layer of nonwoven material joined to an elastomeric material, wherein said second elastically extensible flap is a separate element from said containment assembly and wherein the proximal portion of said second elastically extensible flap is joined to the containment assembly in the first waist region via at least one of a mechanical bond and an adhesive such that said proximal edge of said first elastically extensible flap is disposed inboard of said first side edge of said containment assembly and such that said distal edge of said elastically extensible flap is disposed outboard said first side edge of said containment assembly;
a first elastically extensible waist feature joined to a body facing surface of the containment assembly; and
a refastenable fastening system, the refastenable fastening system comprising:
a landing component, wherein said second waist region comprises said landing component;
a first engaging component comprising a base and a plurality of engaging elements projecting from said base, wherein said first engaging component is joined to the distal portion of the first elastically extensible flap via a plurality of mechanical bonds, wherein said mechanical bonds damage at least some of the engaging elements of said first engaging component;
a second engaging component comprising a base and a plurality of engaging elements projecting from said base, wherein said second engaging component is joined to the distal portion of the second elastically extensible flap via a plurality of mechanical bonds, wherein said mechanical bonds damage at least some of the engaging elements of said second engaging component;
wherein the proximal portion of each of the first and second elastically extensible flaps comprises a high bond zone, wherein the distal portion of each of the first and second elastically extensible flaps comprises a high bond zone and wherein the first engaging component releasably engages a portion of the landing component and the second engaging component releasably engages a portion of the landing component such that the pant-like disposable absorbent article comprises leg openings and a waist opening and is in a pull-on configuration.

17. The pull-on pant-like disposable absorbent article of claim 16 wherein the first and second elastically extensible flaps each comprise a central portion between the proximal and distal portions, wherein the central portion of each of the first and second elastically extensible flaps comprises a low bond zone and wherein the high bond zones in the proximal portions and the high bond zones in the distal portions are less extensible than the low bond zones of the central portions when the first and second elastically extensible flap are subject to a force applied in the transverse direction.

18. The pull-on pant-like disposable absorbent article of claim 1 wherein said landing component comprises first and second landing components that are each joined to said containment assembly, wherein said first engaging component releasably engages said first landing component and said second engaging component releasably engages said second landing component.

* * * * *